United States Patent
Hanafusa

(10) Patent No.: US 8,580,575 B2
(45) Date of Patent: *Nov. 12, 2013

(54) REACTOR PLATE AND REACTION PROCESSING METHOD

(75) Inventor: Nobuhiro Hanafusa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 521 days.

This patent is subject to a terminal disclaimer.

(21) Appl. No.: 12/595,515

(22) PCT Filed: Feb. 29, 2008

(86) PCT No.: PCT/JP2008/053640
§ 371 (c)(1),
(2), (4) Date: Oct. 11, 2009

(87) PCT Pub. No.: WO2008/132871
PCT Pub. Date: Nov. 6, 2008

(65) Prior Publication Data
US 2010/0144054 A1    Jun. 10, 2010

(30) Foreign Application Priority Data

Apr. 13, 2007 (JP) .................................. 2007-106488

(51) Int. Cl.
*B01L 3/00* (2006.01)
(52) U.S. Cl.
USPC ........... 436/180; 436/174; 436/179; 422/505; 422/503; 422/502
(58) Field of Classification Search
None
See application file for complete search history.

(56) References Cited

U.S. PATENT DOCUMENTS

| | | | | |
|---|---|---|---|---|
| 2,847,996 A | * | 8/1958 | Cohen et al. | 604/88 |
| 2004/0191125 A1 | * | 9/2004 | Kellogg et al. | 422/72 |
| 2005/0106066 A1 | | 5/2005 | Saltsman et al. | |
| 2009/0053814 A1 | * | 2/2009 | Patel et al. | 436/8 |

FOREIGN PATENT DOCUMENTS

| | | |
|---|---|---|
| JP | 2000-514928 A | 11/2000 |
| JP | 3452717 B2 | 7/2003 |
| JP | 2004-163104 A | 6/2004 |
| JP | 2004-273830 A | 9/2004 |

(Continued)

OTHER PUBLICATIONS

Stremler, Mark A. et al. "Designing for chaos: applications of chaotic advection at the microscale." Philosophical Transactions of the Royal Society a (2004) 362 1019-1036.*

(Continued)

*Primary Examiner* — Yelena G Gakh
*Assistant Examiner* — Christopher A Hixson
(74) *Attorney, Agent, or Firm* — Cheng Law Group, PLLC

(57) ABSTRACT

Disclosed herein is a reactor plate which prevents the entry of foreign matter from outside and the pollution of an outside environment. The reactor plate includes a sealed reaction well (5), reaction well channels (13, 15, 17) connected to the reaction well (5), and a syringe (51) for sending a liquid to the reaction well channels (13, 15, 17) and the reaction well (5). The syringe (51) has a cylinder (51a), a plunger (51b), and a cover body (51d). The cover body (51d) has flexibility in the sliding direction of the plunger (51b), and is connected to the cylinder (51a) and the plunger (51b) to create a sealed space (51e) enclosed with the cylinder (51a), the plunger (51b), and the cover body (51d). The cover body (51d) is provided to hermetically cut off a part of an inner wall of the cylinder (51a) to be brought into contact with the plunger (51b) from an atmosphere outside the cylinder (51a).

16 Claims, 15 Drawing Sheets

(56) References Cited

FOREIGN PATENT DOCUMENTS

| | | |
|---|---|---|
| JP | 2004-325462 A | 11/2004 |
| JP | 2005-114430 A | 4/2005 |
| JP | 2005-134187 A | 5/2005 |
| JP | 2005-177749 A | 7/2005 |
| JP | 2006-234590 A | 9/2006 |
| WO | WO-98/53311 A2 | 11/1998 |
| WO | WO 2007021812 A1 * | 2/2007 |

OTHER PUBLICATIONS

Weiss, Markus et al. "Syringe size and flow rate affect drug delivery from syringe pumps." Canadian Journal of Anesthesiology (2000) 47 1031-1035.*

International Search Report for the Application No. PCT/JP2008/053640 mailed Jun. 10, 2008.

* cited by examiner

REACTOR PLATE AND REACTION PROCESSING METHOD

BACKGROUND OF THE INVENTION

1. Field of the Invention

The present invention relates to a reactor plate suitable for use in various assays and analyses such as biological and biochemical assays and general chemical analyses in the fields of medical care and chemistry, and a reaction processing method for processing such a reactor plate.

2. Description of the Related Art

As small reactors for use in biochemical assays or general chemical analyses, micro multi-chamber devices are used. Examples of such devices include micro well reactor plates such as a microtiter plate constituted from a plate-shaped substrate having a plurality of wells formed in the surface thereof (see, for example, Patent Document 1) and the like.

Further, as a structure for dispensing a small amount of liquid which can quantitatively treat a small amount of liquid, a structure having a first channel, a second channel, a third channel which is in communication with the first channel through an opening provided in the channel wall of the first channel, and a fourth channel which is in communication with the second channel through an opening provided in the channel wall of the second channel, connects one end of the third channel to the second channel, and has relatively lower capillary attraction than the third channel is developed (see, for example, Patent Documents 2, 3). When such a structure for dispensing a small amount of liquid is used, a liquid introduced into the first channel is drawn into the third channel, and then the liquid remaining in the first channel is removed, and as a result, the liquid having a volume corresponding to the capacity of the third channel is dispensed into the second channel.

Patent Document 1: Japanese Patent Application Laid-open No. 2005-177749
Patent Document 2: Japanese Patent Application Laid-open No. 2004-163104
Patent Document 3: Japanese Patent Application Laid-open No. 2005-114430
Patent Document 3: Japanese Patent No. 3452717

DISCLOSURE OF THE INVENTION

Problem to be Solved by the Invention

When a conventional micro well reactor plate is used, the top surface of the reactor plate is open to the atmosphere. Therefore, there is a fear that foreign matter will enter a sample from outside, or on the other hand, a reaction product will pollute an outside environment.

Further, in the structure for dispensing a small amount of liquid disclosed in Patent Documents 2 and 3, each of the first and second channels has a port for introducing a liquid at each end thereof. However, these ports are open to the atmosphere and, therefore, there is a possibility that a reaction product will leak through the ports and then pollute an outside environment.

Therefore, it is an object of the present invention to provide a reactor plate which can prevent the entry of foreign matter from outside and the pollution of an outside environment, and a reaction processing method using such a reactor plate.

Means for Solving the Problem

The present invention is directed to a reactor plate including a sealed reaction well, a reaction well channel connected to the reaction well, and a syringe for sending a liquid to the reaction well channel and the reaction well. The syringe has a cylinder having a discharge port connected to the reaction well channel, a plunger placed in the cylinder, and a cover body for hermetically cutting off a part of an inner wall of the cylinder to be brought into contact with the plunger from an atmosphere outside the cylinder. The cover body has flexibility in the sliding direction of the plunger, and is connected to the cylinder and the plunger to create a sealed space enclosed with the cylinder, the plunger, and the cover body.

In the reactor plate according to the present invention, since the reaction well is sealed and an internal space of the cylinder connected to the reaction well through the discharge port of the cylinder and the reaction well channel is sealed with the plunger, it is possible to prevent the entry of foreign matter from the outside of the reactor plate and the pollution of an outside environment with a liquid.

Further, since the syringe has the cover body for hermetically cutting off a part of an inner wall of the cylinder to be brought into contact with the plunger from an atmosphere outside the cylinder, it is possible to prevent the entry of foreign matter from outside through a gap between the cylinder and the plunger. In addition, it is also possible to prevent a liquid from leaking out of the reactor plate through the gap between the cylinder and the plunger, thereby preventing the pollution of an outside environment with the liquid.

Here, the cover body needs to have flexibility in at least the sliding direction of the plunger, but may have flexibility also in a direction other than the sliding direction of the plunger.

The reactor plate according to the present invention may further include a variable capacity part whose internal space is sealed and whose internal capacity is passively variable and a syringe air vent channel whose one end is connected to the sealed space and whose other end is connected to the variable capacity part.

The reactor plate according to the present invention may further include a sealed well provided separately from the reaction well, a sealed well channel connected to the sealed well, and a switching valve for connecting the syringe to the reaction well channel or the sealed well channel.

An example of the sealed well includes a sample well for containing a sample liquid.

For example, the sample well may be hermetically sealed with an elastic member which allows a dispensing device having a sharp tip to pass through to form a through hole and which also allows the through hole to be closed by pulling out the dispensing device due to its elasticity.

Further, the sample well may previously contain a liquid for pretreating a sample or a reagent.

The reactor plate according to the present invention may further include one or more reagent wells, each of which is constituted from the sealed well, other than the sample well. The reagent well previously contains a reagent to be used for the reaction of a sample liquid and is sealed with a film, or has an openable and closable cap so that the reagent can be injected thereinto. An example of the film for sealing the reagent well to prevent the leakage of the reagent includes one through which a dispensing device having a sharp tip can pass.

In a case where the reactor plate according to the present invention is intended to be used for gene analysis, the reactor plate preferably includes a gene amplification well which is constituted from the sealed well and used for carrying out gene amplification reaction. The gene amplification well preferably has a shape suitable for controlling a temperature according to a predetermined temperature cycle. It is to be noted that gene amplification can also be carried out in the reaction well.

An example of the switching valve includes a rotary valve. The rotary valve may have a port to be connected to the syringe at the center of rotation. In this case, the syringe may be placed on the rotary valve.

The reactor plate according to the present invention may further include a reaction well air vent channel connected to the reaction well. As a specific example of the channel configuration of the reactor plate according to the present invention, the reaction well channel which is constituted from a groove formed in the contact surface between two members bonded together, or from the groove and a through hole formed in both or one of the members and which includes a main channel connected to the syringe, a metering channel branched off the main channel and having a predetermined capacity, and an injection channel whose one end is connected to the metering channel and whose other end is connected to the reaction well can be mentioned. In this case, the main channel and the reaction well air vent channel can be hermetically sealed, and the injection channel is formed narrower than the metering channel, and does not allow the passage of a liquid at a liquid introduction pressure applied to introduce the liquid into the main channel and the metering channel and at a purge pressure applied to purge the liquid from the main channel but allows the passage of the liquid at a pressure higher than the liquid introduction pressure and the purge pressure.

Here, the phrase "the injection channel is formed narrower than the metering channel" means that in a case where the injection channel is constituted from a plurality of channels, each of the channels constituting the injection channel is formed narrower than the metering channel.

The present invention is also directed to a reaction processing method using the reactor plate according to the present invention having the channel configuration described above as an example of a channel configuration, the method including filling the main channel and the metering channel with a liquid at the introduction pressure, purging the liquid from the main channel by flowing a gas through the main channel while allowing the liquid to remain in the metering channel, and injecting the liquid contained in the metering channel into the reaction well through the injection channel by creating a positive pressure higher than the introduction pressure in the main channel, or by creating a negative pressure in the reaction well, or by creating a positive pressure higher than the introduction pressure in the main channel and creating a negative pressure in the reaction well.

In the channel configuration described above as an example of a channel configuration, the contact angle of the injection channel with a water drop is, for example, 90° or larger, and the area of an interface between the injection channel and the metering channel is, for example, 1 to 10,000,000 $\mu m^2$ (square micrometers). It is to be noted that in a case where the injection channel is constituted from a plurality of channels, the phrase "the area of an interface between the injection channel and the metering channel" means the area of an interface between each of the channels constituting the injection channel and the metering channel.

The reactor plate according to the present invention may include a plurality of the reaction wells. In this case, the metering channel and the injection channel may be provided for each of the reaction wells, and the plurality of metering channels may be connected to the main channel.

Further, a projecting portion may be provided so as to project from a top inner surface of the reaction well. In this case, the other end of the injection channel is located at the tip of the projecting portion. The projecting portion includes one having a proximal end and a distal end narrower than the proximal end.

The reaction well can be used for carrying out at least any one of color reaction, enzymatic reaction, fluorescence reaction, chemiluminescence reaction, and bioluminescence reaction.

In a case where the reactor plate according to the present invention is intended to be used for measuring a gene-containing sample, a sample previously subjected to gene amplification reaction may be introduced into the reactor plate, or a gene amplification reagent may be previously contained in the reaction well or the reactor plate may be designed to allow a gene amplification reagent to be dispensed into the reaction well so that gene amplification reaction can be carried out in the reaction well of the reactor plate.

Examples of the gene amplification reaction include PCR method and LAMP method. As PCR method for amplifying DNA, a method is proposed for directly subjecting a sample such as blood to PCR reaction without pretreating the sample. More specifically, this method is a nucleic acid synthesis method for amplifying a target gene contained in a gene-containing sample by adding a gene-containing body contained in the gene-containing sample or the gene-containing sample itself and then adjusting the pH of the thus obtained reaction mixture to 8.5 to 9.5 (25° C.) (see Patent Document 4).

The reaction well may be made of an optically-transparent material so that optical measurement can be carried out from the bottom of the reaction well or from above the reaction well.

In a case where a liquid to be introduced into the reaction well channel contains a gene, the reaction well may contain a probe which reacts with the gene.

Further, the probe may be fluorescently-labeled.

Effect of the Invention

As described above, the reactor plate according to the present invention includes a sealed reaction well, a reaction well channel connected to the reaction well, and a syringe for sending a liquid to the reaction well channel and the reaction well, the reaction well is sealed, and an internal space of the cylinder connected to the reaction well through the discharge port of the cylinder and the reaction well channel is sealed with the plunger. Therefore, it is possible to prevent the entry of foreign matter from the outside of the reactor plate and the pollution of an outside environment with a liquid.

Further, the syringe has a cylinder having a discharge port connected to the reaction well channel, a plunger placed in the cylinder, and a cover body for hermetically cutting off a part of an inner wall of the cylinder to be brought into contact with the plunger from an atmosphere outside the cylinder, and the cover body has flexibility in the sliding direction of the plunger and is connected to the cylinder and the plunger to create a sealed space enclosed with the cylinder, the plunger, and the cover body. Therefore, it is possible to prevent the entry of foreign matter from outside through a gap between the cylinder and the plunger. In addition, it is also possible to prevent a liquid from leaking out of the reactor plate through the gap between the cylinder and the plunger, thereby preventing the pollution of an outside environment with the liquid.

In a case where the reactor plate according to the present invention is intended to be used for measuring a gene-containing sample, the sample injected into the reactor plate and then introduced into the reaction well can be processed in a closed system. Therefore, it is possible to prevent the pollution of an environment outside the reactor plate and the contamination of the sample with foreign matter coming from outside the reactor plate.

The reactor plate according to the present invention may further include a variable capacity part whose internal space is sealed and whose internal capacity is passively variable and a syringe air vent channel whose one end is connected to the sealed space and whose other end is connected to the variable capacity part. This makes it possible to cut off the sealed space from an atmosphere outside the reactor plate and to relieve a pressure change in the sealed space caused by a change in the internal capacity of the sealed space during the sliding of the plunger, thereby making it possible to smoothly slide the plunger.

The reactor plate according to the present invention may further include a sealed well provided separately from the reaction well, a sealed well channel connected to the sealed well, and a switching valve for connecting the syringe to the reaction well channel or the sealed well channel.

For example, by providing a sample well for containing a sample liquid as the sealed well, it is possible to eliminate the necessity to separately prepare a well for containing a sample.

Further, the sample well may be hermetically sealed with an elastic member which allows a dispensing device having a sharp tip to pass through to form a through hole and which also allows the through hole to be closed by pulling out the dispensing device due to its elasticity. This makes it possible to inject a sample liquid into the sample well sealed with the elastic member and to prevent the sample liquid injected into the sample well from leaking out of the sample well.

Further, the sample well may previously contain a liquid for pretreating a sample or a reagent. This makes it possible to eliminate the necessity to dispense a liquid for pretreating a sample or a reagent into the sample well.

The reactor plate according to the present invention may further include one or more reagent wells, each of which is constituted from the sealed well, other than the sample well. By allowing the reagent well to previously contain a reagent to be used for the reaction of a sample liquid and sealing it with a film or by allowing the reagent well to have an openable and closable cap so that the reagent can be injected thereinto, it is possible to eliminate the necessity to separately prepare a well for containing the reagent.

The reactor plate according to the present invention may further include a gene amplification well which is constituted from the sealed well and used for carrying out gene amplification reaction. By providing such a gene amplification well, it is possible to amplify a target gene in the reactor plate by gene amplification reaction such as PCR method or LAMP method even when a sample liquid contains only a very small amount of the target gene, thereby increasing analytical precision.

The reactor plate according to the present invention may further include a sealed well channel connected to the sealed well, a syringe for sending a liquid, and a switching valve for connecting the syringe to the main channel or the sealed well channel. In this case, a liquid contained in the sealed well can be injected into the main channel with the syringe and the switching valve.

The switching valve may be a rotary valve. In this case, by providing a port to be connected to the syringe at the center of rotation of the rotary valve, it is possible to simplify a channel configuration.

Further, by providing a port to be connected to the syringe at the center of rotation of the rotary valve and placing the syringe on the rotary valve, it is possible to shorten or eliminate a channel between the port and the syringe, thereby simplifying the structure of the reactor plate. In addition, it is also possible to effectively utilize a region on the switching valve, thereby making it possible to make the planar size of the reactor plate smaller as compared to a case where the syringe is placed in a region other than the region on the switching valve.

The reactor plate according to the present invention may further include a reaction well air vent channel connected to the reaction well. As a specific example of the channel configuration of the reactor plate according to the present invention, the reaction well channel which is constituted from a groove formed in the contact surface between two members bonded together, or from the groove and a through hole formed in both or one of the members and which includes a main channel connected to the syringe, a metering channel branched off the main channel and having a predetermined capacity, and an injection channel whose one end is connected to the metering channel and whose other end is connected to the reaction well can be mentioned. In this case, the main channel and the reaction well air vent channel can be hermetically sealed, and the injection channel is formed narrower than the metering channel, and does not allow the passage of a liquid at a liquid introduction pressure applied to introduce the liquid into the main channel and the metering channel and at a purge pressure applied to purge the liquid from the main channel but allows the passage of the liquid at a pressure higher than the liquid introduction pressure and the purge pressure. By carrying out the reaction processing method according to the present invention with the reactor plate according to the present invention, it is possible to prevent the entry of foreign matter from the outside of the reactor plate and the pollution of an outside environment with a liquid.

Further, by providing the reaction well air vent channel connected to the reaction well, it is possible to move a gas between the reaction well and the reaction well air vent channel when a liquid is injected into the reaction well through the injection channel, thereby making it possible to smoothly inject a liquid into the reaction well. The reaction well air vent channel can also be used to suck a gas contained in the reaction well to decompress the reaction well to inject a liquid into the reaction well.

In the channel configuration described above as an example of a channel configuration, the contact angle of the metering channel and the injection channel with a water droplet is preferably 90° or larger, and the area of an interface between the injection channel and the metering channel is preferably 1 to 10,000,000 $\mu m^2$. This makes it difficult for a liquid to enter the injection channel when the liquid is introduced into the main channel and the metering channel, thereby making it possible to increase an introduction pressure applied to introduce a liquid into the main channel and the metering channel.

The reactor plate according to the present invention may include a plurality of the reaction wells. In this case, by providing the metering channel and the injection channel for each of the reaction wells and connecting the plurality of metering channels to the main channel, it is possible to introduce a liquid into the plurality of metering channels one after another and then simultaneously inject the liquid into the plurality of reaction wells through the injection channels.

Further, a projecting portion may be provided so as to project from a top inner surface of the reaction well. In this case, the other end of the injection channel is located at the tip of the projecting portion. By allowing the projecting portion to have a proximal end and a distal end narrower than the proximal end, a liquid to be injected into the reaction well through the injection channel can be easily dropped into the reaction well.

In a case where the reactor plate according to the present invention is intended to be used for measuring a gene-containing sample, the reactor plate may be designed to allow gene amplification reaction to be carried out in the reaction well. This makes it possible to eliminate the necessity to prepare a sample which has been subjected to gene amplification reaction outside the reactor plate.

The reaction well may be made of an optically-transparent material so that optical measurement can be carried out from the bottom of the reaction well or from above the reaction well. This makes it possible to optically measure a liquid contained in the reaction well without transferring the liquid into another well.

In a case where a liquid to be introduced into the reaction well channel contains a gene, the reaction well may contain a probe which reacts with the gene. This makes it possible to detect a gene having a base sequence corresponding to the probe in the reaction well.

Figure 1A:
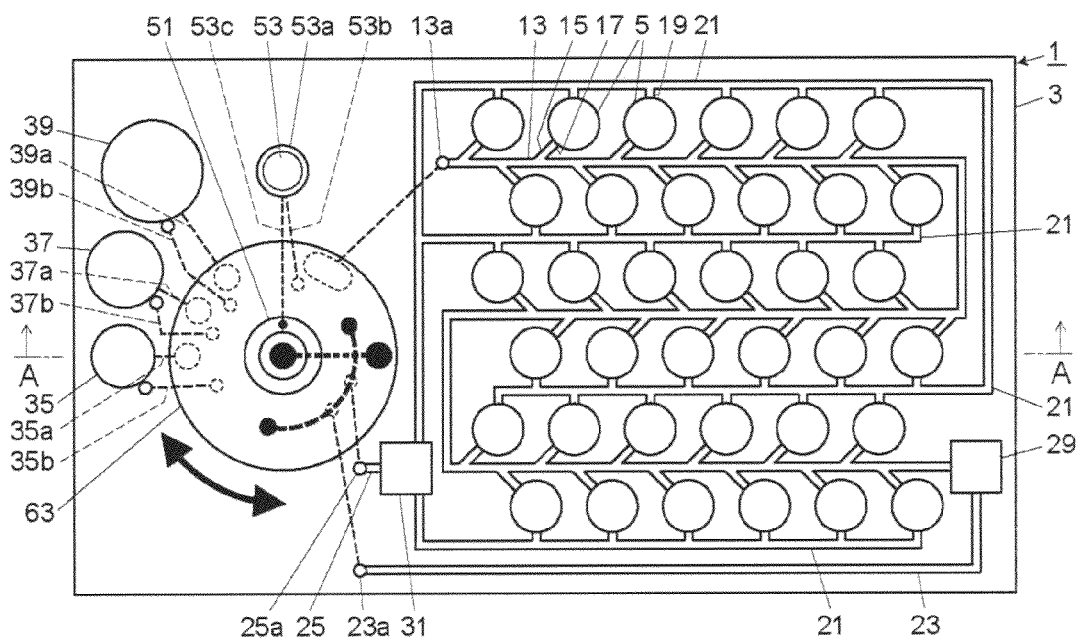
FIG. 1A is a schematic plan view of one embodiment of a reactor plate according to the present invention.

DESCRIPTION OF THE REFERENCE NUMERALS 1 reactor plate
3 well base
5 reaction well
11 channel base
13 main channel
15 metering channel
17 injection channel
19, 21 reaction well air vent channel
35 sample well
35b, 35d, 35e sample well air vent channel
37 reagent well
37b, 37d, 37e reagent well air vent channel
39 well for air suction
39b, 39d, 39e air vent channel for well for air suction
51, 87 syringe
51a, 87a cylinder
51b, 87b plunger
51d, 87d cover body
51e, 87e sealed space
53 bellows (variable capacity part)
53c syringe air vent channel
63, 95 switching valve
73 channel spacer
75 projecting portion
77 injection channel
79 reaction well air vent channel

DETAILED DESCRIPTION OF THE INVENTION

Figure 1B:
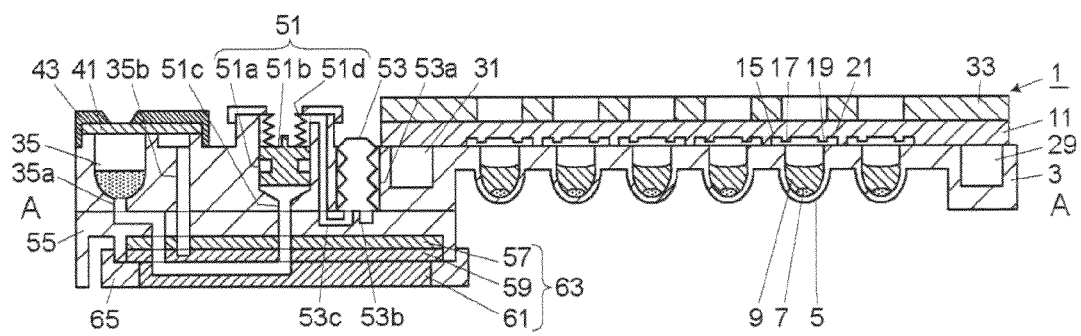
FIG. 1B is a schematic sectional view taken along the A-A line in FIG. 1A, which further includes the sectional views of a bellows, drain spaces, a metering channel, an injection channel, and a sample well air vent channel.
Figure 1C:
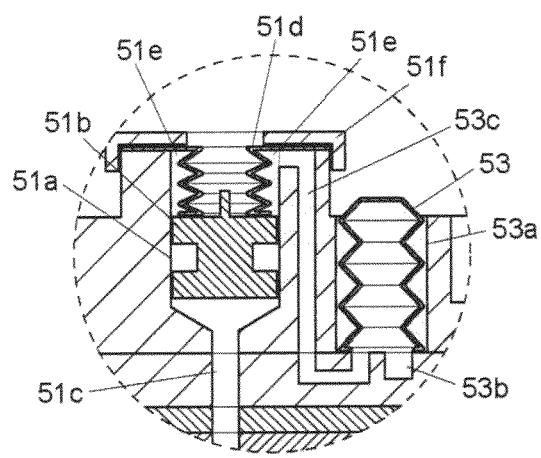
FIG. 1C is a schematic expanded sectional view of a syringe 51 and the bellows 53 of the reactor plate in the embodiment shown in FIG. 1A and their vicinity.
Figure 2:
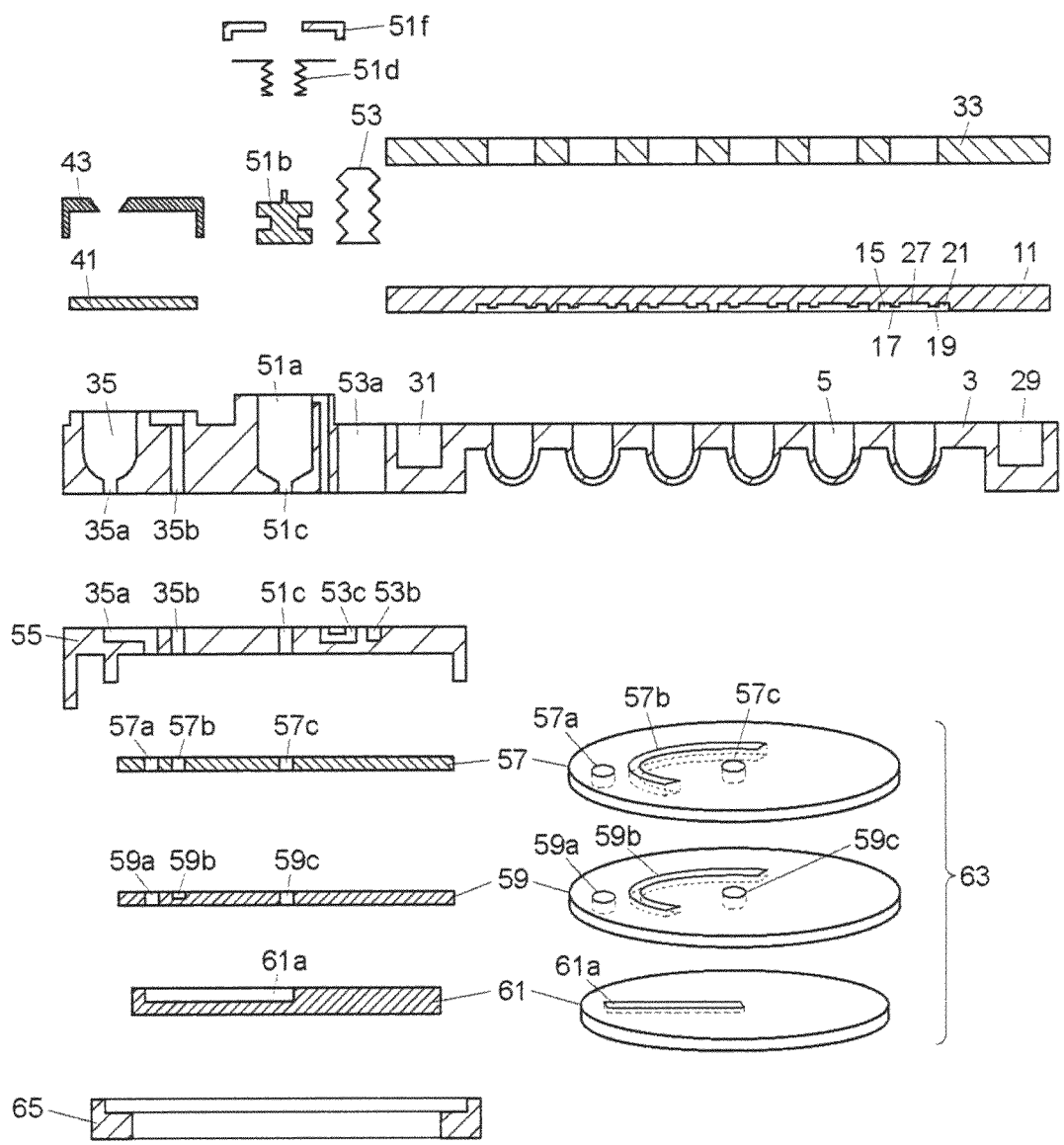
FIG. 2 shows an exploded sectional view of the reactor plate in the embodiment shown in FIG. 1A and a schematic exploded perspective view of a switching valve.
Figure 3A:
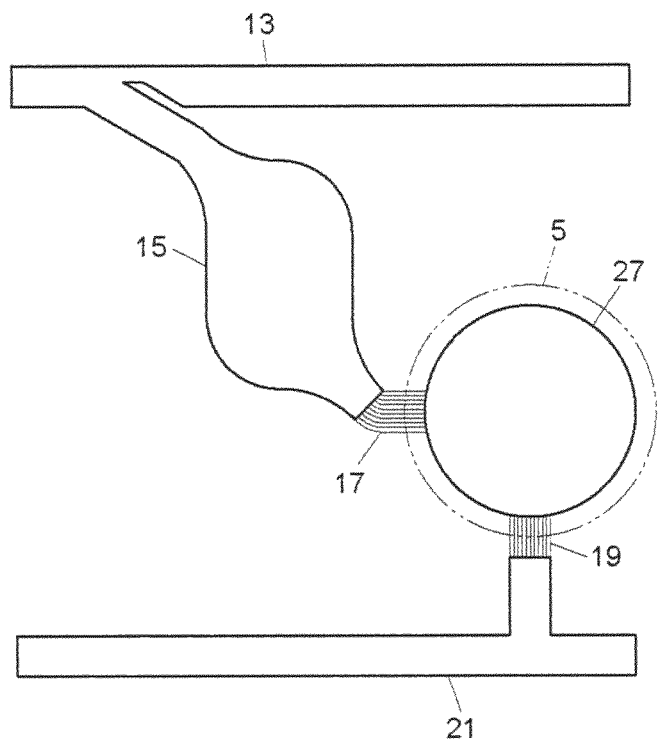
FIG. 3A is a schematic plan view of one reaction well of the reactor plate in the embodiment shown in FIG. 1A and its vicinity.
Figure 3B:
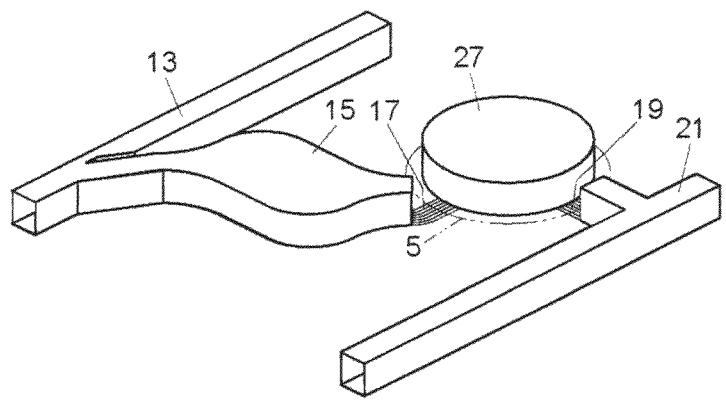
FIG. 3B is a schematic perspective view of one reaction well of the reactor plate in the embodiment shown in FIG. 1A and its vicinity.
Figure 3C:
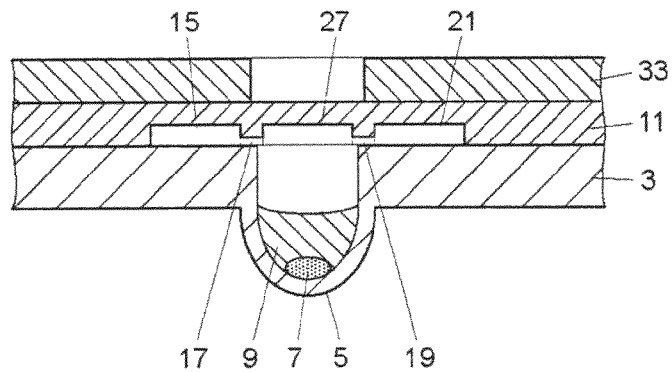
FIG. 3C is a schematic sectional view of one reaction well of the reactor plate in the embodiment shown in FIG. 1A and its vicinity.
Figure 4A:
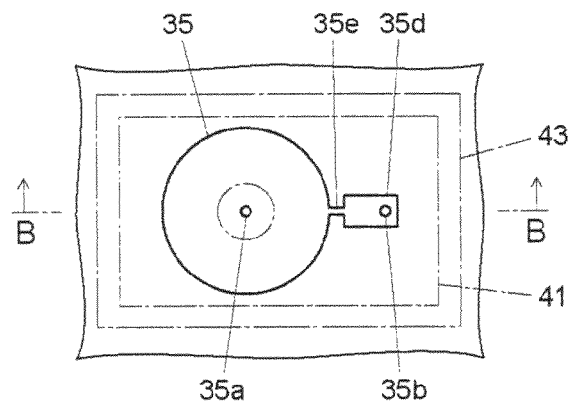
FIG. 4A is a schematic expanded plan view of a sample well of the reactor plate in the embodiment shown in FIG. 1A.
Figure 4B:
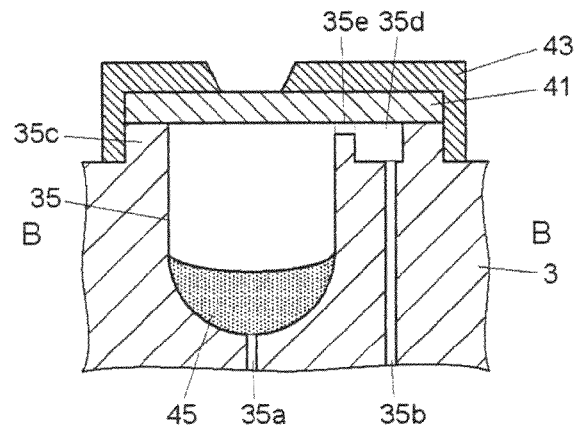
FIG. 4B is a sectional view taken along the B-B line in FIG. 4A.
Figure 5A:
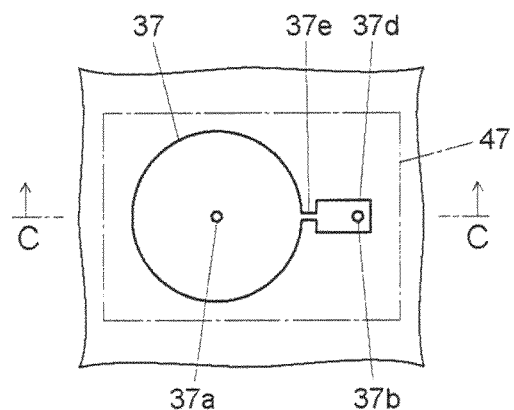
FIG. 5A is an expanded plan view of a reagent well of the reactor plate in the embodiment shown in FIG. 1A.
Figure 5B:
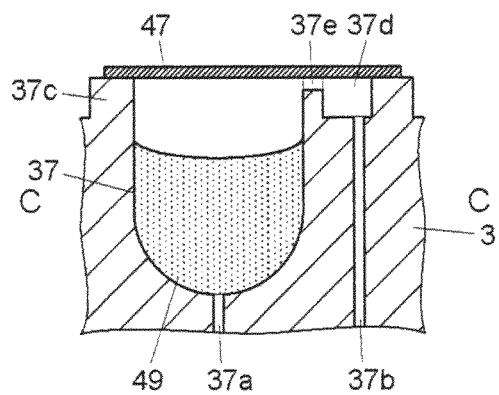
FIG. 5B is a sectional view taken along the C-C line in FIG. 5A.
Figure 6A:
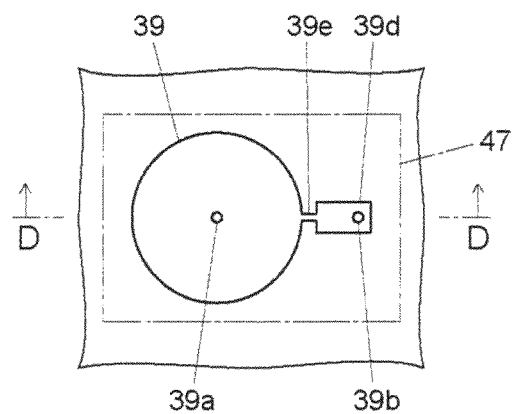
FIG. 6A is an expanded plan view of a well for air suction of the reactor plate in the embodiment shown in FIG. 1A.
Figure 6B:
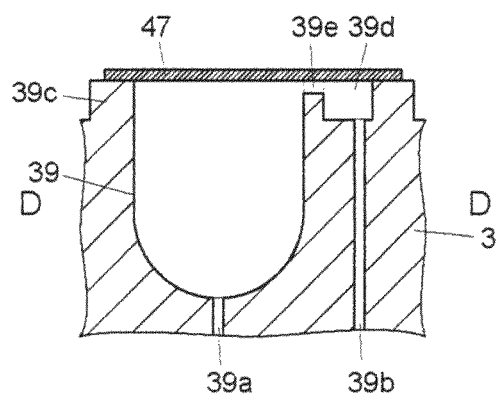
FIG. 6B is a sectional view taken along the D-D line in FIG. 6A.

FIG. 1A is a schematic plan view of one embodiment of a reactor plate according to the present invention, and FIG. 1B is a schematic sectional view taken along the A-A line in FIG. 1A, which further includes the sectional views of a metering channel 15, an injection channel 17, reaction well air vent channels 19 and 21, a liquid drain space 29, an air drain space 31, and a bellows 53. FIG. 1C is a schematic expanded sectional view of a syringe 51 and the bellows 53 of the reactor plate in the embodiment shown in FIG. 1A and their vicinity. FIG. 2 shows an exploded sectional view of the reactor plate in the embodiment shown in FIG. 1A and a schematic exploded perspective view of a switching valve. FIGS. 3A to 3C are a schematic plan view, a schematic perspective view, and a schematic sectional view of one reaction well of the reactor plate in the embodiment shown in FIG. 1A and its vicinity, respectively. FIG. 4A is an expanded plan view of a sample well, and FIG. 4B is a sectional view taken along the B-B line in FIG. 4A. FIG. 5A is an expanded plan view of a reagent well, and FIG. 5B is a sectional view taken along the C-C line in FIG. 5A. FIG. 6A is an expanded plan view of a well for air suction, and FIG. 6B is a sectional view taken along the D-D line in FIG. 6A. With reference to FIGS. 1A to 6B, the reactor plate according to one embodiment of the present invention will be described.

A reactor plate 1 includes a plurality of reaction wells 5 each having an opening in one surface of a well base 3. In the reactor plate 1 according to this embodiment of the present invention, the reaction wells 5 are arranged in an array of 6 rows and 6 columns in a staggered format. In each of the reaction wells 5, a reagent 7 and a wax 9 are contained.

The material of the well base 3 including the reaction wells 5 is not particularly limited. However, in a case where the reactor plate 1 is intended to be disposable, the material of the well base 3 is preferably a cheaply-available material. Preferred examples of such a material include resin materials such as polypropylene and polycarbonate. In a case where the reactor plate 1 is intended to be used to detect a substance in the reaction well 5 by absorbance, fluorescence, chemiluminescence, or bioluminescence, the container base 3 is preferably made of an optically-transparent resin so that optical detection can be carried out from the bottom of the reaction well 5. Particularly, in a case where the reactor plate 1 is intended to be used for fluorescence detection, the container base 3 is preferably made of a low self-fluorescent (i.e., fluorescence emitted from a material itself is weak) and optically-transparent resin, such as polycarbonate. The thickness of the well base 3 is in a range of 0.2 to 4.0 mm (millimeters), preferably in a range of 1.0 to 2.0 mm. From the viewpoint of low self-fluorescence, the thickness of the well base 3 for fluorescence detection is preferably small.

Referring to FIGS. 1A, 1B, 1C, 3A, 3B and 3C, a channel base 11 is provided on the well base 3 so as to cover a region where the reaction wells 5 are arranged. The channel base 11 is made of, for example, PDMS (polydimethylsiloxane) or silicone rubber. The thickness of the channel base 11 is, for example, from 1.0 to 5.0 mm. The channel base 11 has a groove in its surface which is in contact with the well base 3. The groove and the surface of the well base 3 together form a main channel 13, the metering channel 15, the injection channel 17, the reaction well air vent channels 19 and 21, and drain space air vent channels 23 and 25. The main channel 13, the metering channel 15, and the injection channel 17 constitute a reaction well channel. In the surface of the channel base 11 which is in contact with the well base 3, a recess 27 is also provided so as to be located above each of the reaction wells 5. It is noted that, in FIG. 1A and FIGS. 3A and 3B, the channel base 11 is not shown, and only the groove and recess provided in the channel base 11 are shown.

The main channel 13 is constituted from one channel, and is therefore bent so as to run in the vicinity of all the reaction wells 5. One end of the main channel 13 is connected to a channel 13a constituted from a through hole provided in the well base 3. The channel 13a is connected to a port of a switching valve 63 (which will be described later). The other end of the main channel 13 is connected to the liquid drain space 29 provided in the well base 3. The main channel 13 is constituted from a groove having a depth of, for example, 400 μm (micrometers) and a width of, for example, 500 μm. It is noted that a part of the main channel 13 having a predetermined length (e.g., 250 μm) and located downstream of a position, to which the metering channel 15 is connected, has a width smaller than that of the other part of the main channel 13, and the width of such a part is, for example, 250 μm.

The metering channel 15 branches off the main channel 13, and is provided for each of the reaction wells 5. The end of the metering channel 15 on the opposite side from the main channel 13 is located in the vicinity of the reaction well 5. The depth of a groove constituting the metering channel 15 is, for example, 400 μm. The metering channel 15 is designed to have a predetermined internal capacity of, for example, 2.5 μL (microliters). A part of the metering channel 15 connected to the main channel 13 has a width larger than that of the above-described narrow part of the main channel 13 (e.g., 500 μm). Therefore, at a position where the metering channel 15 branches off the main channel 13, the resistance to the flow of a liquid coming from one end of the main channel 13 is larger in the main channel 13 than in the metering channel 15. For this reason, the liquid coming from one end of the main channel 13 first flows into the metering channel 15 to fill the metering channel 15, and then flows downstream through the narrow part of the main channel 13.

The injection channel 17 is also provided for each of the reaction wells 5. One end of the injection channel 17 is connected to the metering channel 15, and the other end of the injection channel 17 is connected to the recess 27 located above the reaction well 5 so as to be led to the space above the reaction well 5. The injection channel 17 is designed to have a size allowing the liquid-tightness of the reaction well 5 to be maintained in a state where there is no difference between the pressure in the reaction well 5 and the pressure in the injection channel 17. According to the present embodiment, the injection channel 17 is constituted from a plurality of grooves, and each groove has a depth of, for example, 10 μm and a width of, for example, 20 μm, and the pitch between the adjacent grooves is, for example, 20 μm, and the thirteen grooves are provided in a region having a width of 500 μm. In this case, the area of an interface between the groove constituting the injection channel 17 and the metering channel 15, that is, the cross-sectional area of the groove constituting the injection channel 17 is 200 μm². The recess 27 has a depth of, for example, 400 μm, and has a circular planar shape smaller than that of the reaction well 5.

The reaction well air vent channel 19 is provided for each of the reaction wells 5. One end of the reaction well air vent channel 19 is connected to the recess 27, which is located above the reaction well 5, at a position different from the position, to which the injection channel 17 is connected, so as to be located above the reaction well 5. The reaction well air vent channel 19 is designed to have a size allowing the liquid-tightness of the reaction well 5 to be maintained in a state where there is no difference between the pressure in the reaction well 5 and the pressure in the reaction well air vent channel 19. The other end of the reaction well air vent channel 19 is connected to the reaction well air vent channel 21. According to the present embodiment, the reaction well air vent channel 19 is constituted from a plurality of grooves, and each groove has a depth of, for example, 10 μm and a width of, for example, 20 μm, and the pitch between the adjacent grooves is, for example, 20 μm, and the thirteen grooves are provided in a region having a width of 500 μm.

The reactor plate according to the present embodiment has plurality a of the reaction well air vent channels 21. To each of the reaction well air vent channels 21, the plurality of reaction well air vent channels 19 are connected. These reaction well air vent channels 21 are provided to connect the reaction well air vent channels 19 to the air drain space 31 provided in the well base 3. Each of the reaction well air vent channels 21 is constituted from a groove having a depth of, for example, 400 μm and a width of, for example, 500 μm.

The drain space air vent channel 23 is provided to connect the liquid drain space 29 to a port of the switching valve 63 (which will be described later). One end of the drain space air vent channel 23 is located above the liquid drain space 29. The other end of the drain space air vent channel 23 is connected to a channel 23a constituted from a through hole provided in the well base 3. The channel 23a is connected to a port of the switching valve 63 (which will be described later). The drain space air vent channel 23 is constituted from a groove having a depth of, for example, 400 μm and a width of, for example, 500 μm.

The drain space air vent channel 25 is provided to connect the air drain space 31 to a port of the switching valve 63 (which will be described later). One end of the drain space air vent channel 25 is located above the air drain space 31. The other end of the drain space air vent channel 25 is connected to a channel 25a constituted from a through hole provided in the well base 3. The channel 25a is connected to a port of the switching valve 63 (which will be described later). The drain space air vent channel 25 is constituted from a groove having a depth of, for example, 400 μm and a width of, for example, 500 μm.

On the channel base 11, a channel cover 33 (not shown in FIG. 1A) is provided. The channel cover 33 is provided to fix the channel base 11 to the well base 3. The channel cover 33 has a through hole formed to be located above each of the reaction wells 5.

Referring to FIGS. 1A, 1B, 1C, 4A and 4B, in the well base 3, a sample well 35, a reagent well 37, and a well 39 for air suction are provided at positions other than the positions of a region where the reaction wells 5 are arranged, and the drain spaces 29 and 31. The sample well 35, the reagent well 37, and the well 39 for air suction constitute sealed wells of the reactor plate according to the present invention.

In the well base 3, a sample channel 35a constituted from a through hole extending from the bottom of the sample well 35 to the back surface of the well base 3 and a sample well air vent channel 35b constituted from a through hole extending from the top surface to the back surface of the well base 3 are provided in the vicinity of the sample well 35. On the well base 3, a projecting portion 35c is provided so as to surround an opening of the sample well 35. In the projecting portion 35c, a sample well air vent channel 35d constituted from a through hole is provided so as to be located above the sample well air vent channel 35b. In the surface of the projecting portion 35c, a sample well air vent channel 35e which allows the sample well 35 to communicate with the sample well air vent channel 35d is provided.

The sample well air vent channel 35e is constituted from one or more narrow holes, and each narrow hole has a width of, for example, 5 to 200 μm and a depth of, for example, 5 to 200 μm. The sample well air vent channel 35e is provided to maintain the liquid-tightness of the sample well 35 in a state where there is no difference between the pressure in the sample well 35 and the pressure in the sample well air vent channel 35d. On the projecting portion 35c, a septum 41 as an elastic member to cover the sample well 35 and the air vent channel 35d is provided. The septum 41 is made of an elastic material such as silicone rubber or PDMS. Therefore, a dispensing device having a sharp tip can pass through the septum 41 to form a through hole, but the through hole can be closed by pulling the dispensing device out of the septum 41 due to its elasticity. On the septum 41, a septum stopper 43 for fixing the septum 41 is provided. The septum stopper 43 has an opening located above the sample well 35. According to the present embodiment, a reagent 45 is previously contained in the sample well 35.

As shown in FIGS. 5A and 5B, in the well base 3, a reagent channel 37a constituted from a through hole extending from the bottom of the reagent well 37 to the back surface of the well base 3 and a reagent well air vent channel 37b constituted from a through hole extending from the top surface to the back surface of the well base 3 are provided in the vicinity of the reagent well 37. On the well base 3, a projecting portion 37c is provided so as to surround an opening of the reagent well 37. In the projecting portion 37c, a reagent well air vent channel 37d constituted from a through hole is provided so as to be located above the reagent well air vent channel 37b. In the surface of the projecting portion 37c, a reagent well air vent channel 37e which allows the reagent well 37 to communicate with the reagent well air vent channel 37d is provided.

The reagent well air vent channel 37e is constituted from one or more narrow holes, and each narrow hole has a width of, for example, 5 to 200 μm and a depth of, for example, 5 to 200 μm. The reagent well air vent channel 37e is provided to maintain the liquid-tightness of the reagent well 37 in a state where there is no difference between the pressure in the reagent well 37 and the pressure in the reagent well air vent channel 37d. On the projecting portion 37c, a film 47 made of, for example, aluminum to cover the reagent well 37 and the air vent channel 37d is provided. In the reagent well 37, dilution water 49 is contained.

As shown in FIGS. 6A and 6B, the well 39 for air suction has the same structure as the reagent well 37. That is, in the well base 3, a channel 39a for air suction constituted from a through hole extending from the bottom of the well 39 for air suction to the back surface of the well base 3 and an air vent channel 39b for the well for air suction constituted from a through hole extending from the top surface to the back surface of the well base 3 are provided in the vicinity of the well 39 for air suction. On the well base 3, a projecting portion 39c having air vent channels 39d and 39e for the well for air suction is provided so as to surround an opening of the well 39 for air suction. On the projecting portion 39c, a film 47 made of, for example, aluminum is provided. The well 39 for air suction contains neither a liquid nor a solid, but is filled with air.

Referring to FIGS. 1A, 1B, 1C, and 2, a syringe 51 is provided in the surface of the well base 3 at a position other than the positions of a region where the reaction wells 5 are arranged, the drain spaces 29 and 31, and the wells 35, 37 and 39. The syringe 51 is constituted from a cylinder 51a provided in the well base 3 and having a discharge port provided at the bottom thereof, a plunger 51b placed in the cylinder 51a, and a cover body 51d. In the well base 3, a syringe channel 51c extending from the discharge port of the cylinder 51a to the back surface of the well base 3 is provided.

The cover body 51d has flexibility in the sliding direction of the plunger 51b, and is connected to the cylinder 51a and the plunger 51b. The cover body 51d is provided to create a sealed space 51e to hermetically cut off a part of an inner wall of the cylinder 51a to be brought into contact with the plunger 51b from an atmosphere outside the cylinder 51a. The sealed space 51e is enclosed with the cylinder 51a, the plunger 51b, and the cover body 51d. One end of the cover body 51d connected to the cylinder 51a is hermetically fixed to the upper end of the cylinder 51a by a cylinder cap 51f. On the other hand, the other end of the cover body 51d connected to the plunger 51b is hermetically connected to the upper surface of the plunger 51b by an adhesive. However, a method for connecting the cover body 51d to the cylinder 51a and the plunger 51b is not limited to the method described above, and the connecting positions of the cover body 51d are not limited to those described above.

As described above, the cover body 51d is connected to the cylinder 51a and the plunger 51b to create a sealed space 51e enclosed with the cylinder 51a, the plunger 51b, and the cover body 51d and, therefore, it is possible to prevent the entry of foreign matter from outside through a gap between the cylinder 51a and the plunger 51b. In addition, it is also possible to prevent the leakage of a liquid through the gap between the cylinder 51a and the plunger 51b, thereby preventing the pollution of an outside environment with the liquid. It is to be noted that as described above, since the cover body 51d has flexibility in the sliding direction of the plunger 51b, the plunger 51b can be slidably moved.

According to the present embodiment, the plunger 51b and the cover body 51d are provided as separate members, but the plunger and the cover body may be integrally molded. The plunger and the cover body can be integrally molded using, for example, silicone rubber.

In the well base 3, the bellows 53 is also provided at a position other than the positions of a region where the reaction wells 5 are arranged, the drain spaces 29 and 31, the wells 35, 37, and 39, and the syringe 51. The bellows 53 has a sealed internal space, and the internal capacity of the bellows 53 is passively variable by extraction and contraction. The bellows 53 is placed in, for example, a through hole 53a provided in the well base 3.

A well bottom 55 is attached to the back surface of the well base 3 at a position other than the position of a region where the reaction wells 5 are arranged. In the well bottom 55, an air vent channel 53b is provided at a position allowing the air vent channel 53b to communicate with the bellows 53. The bellows 53 is connected to the well bottom 55 so as to be in close contact with the surface of the well bottom 55. The well bottom 55 is provided to guide the channels 13a, 23a, 25a, 35a, 35b, 37a, 37b, 39a, 39b, 51c, and 53b to predetermined port positions.

In the well base 3 and the well bottom 55, a syringe air vent channel 53c whose one end is connected to the sealed space 51e and whose other end is connected to the bellows 53 is provided. In FIG. 1A, the syringe air vent channel 53c is not shown.

As described above, the reactor plate 1 has the syringe air vent channel 53c whose one end is connected to the sealed space 51e and whose other end is connected to the bellows 53 and, therefore, it is possible to cut off the sealed space 51e from an atmosphere outside the reactor plate 1 and to relieve a pressure change in the sealed space 51e caused by a change in the internal capacity of the sealed space 51e during the sliding of the plunger 51b, thereby making it possible to smoothly slide the plunger 51b.

On the surface of the reaction well bottom 55 located on the opposite side from the well base 3, the rotary switching valve 63 is provided. The switching valve 63 is constituted from disk-shaped sealing plate 57, rotor upper 59, and rotor base 61. The switching valve 63 is attached to the well bottom 55 by means of a lock 65.

The sealing plate 57 has a through hole 57a, a through groove 57b, and a through hole 57c. The through hole 57a is provided in the vicinity of the peripheral portion of the sealing plate 57, and is connected to any one of the channels 13a, 35a, 37a, and 39a. The through groove 57b is provided inside the through hole 57a and on a circle concentric with the sealing plate 57, and is connected to at least two of the channels 23a, 25a, 35b, 37b, 39b, and 53b. The through hole 57c is provided at the center of the sealing plate 57, and is connected to the syringe channel 51c.

The rotor upper 59 has a through hole 59a, a groove 59h, and a through hole 59c. The through hole 59a is provided at a position corresponding to the through hole 57a provided in the sealing plate 57. The groove 59b is provided in the surface of the rotor upper 59 so as to correspond to the through groove 57b provided in the sealing plate 57. The through hole 59c is provided at the center of the rotor upper 59.

The rotor base 61 has a groove 61a. The groove 61a is provided in the surface of the rotor base 61 to connect the through hole 59a provided in the peripheral portion of the rotor upper 59 and the through hole 59c provided at the center of the rotor upper 59 to each other.

By rotating the switching valve 63, the syringe channel 51c is connected to any one of the channels 13a, 35a, 37a, and 39a, and at the same time, the air vent channel 53b is also connected to at least any one of the channels 23a, 25a, 35b, 37b, and 39b.

The switching valve 63 shown in FIG. 1A is in its initial state where the syringe channel 51c is not connected to any one of the channels 13a, 35a, 37a, and 39a, and the air vent channel 53b is not connected to any one of the channels 23a, 25a, 35b, 37b, and 39b, either.

As described above, the injection channel 17 provided in the reactor plate 1 is designed so that the liquid-tightness of the reaction well 5 is maintained in a state where there is no difference between the pressure in the injection channel 17 and the pressure in the reaction well 5. The reaction well air vent channel 19 is also designed so that the liquid-tightness of the reaction well 5 is maintained in a state where there is no difference between the pressure in the reaction well 5 and the pressure in the reaction well air vent channel 19. The main channel 13 constituting the reaction well channel, the liquid drain space 29 connected to the main channel 13, and the drain space air vent channel 23 can be hermetically sealed by switching of the switching valve 63. The wells 35, 37, and 39 are sealed with the septum 41 or the film 47. The channels 35a, 35b, 37a, 37b, 39a, and 39b connected to the wells 35, 37, and 39, respectively, can be hermetically sealed by switching the switching valve 63. One end of the air vent channel 53b is connected to the bellows 53 and, therefore, the air vent channel 53b is hermetically sealed. As described above, the wells and channels in the reactor plate 1 constitute a closed system. It is noted that even in a case where the reactor plate 1 does not have the bellows 53 and the air vent channel 53b is connected to the atmosphere outside the reactor plate 1, the air vent channel 53b can be cut off from the wells and the channels other than the air vent channel 53b provided in the reactor plate 1 by switching of the switching valve 63 and, therefore, the wells for containing a liquid and the channels for flowing a liquid can be hermetically sealed.

Figure 7:
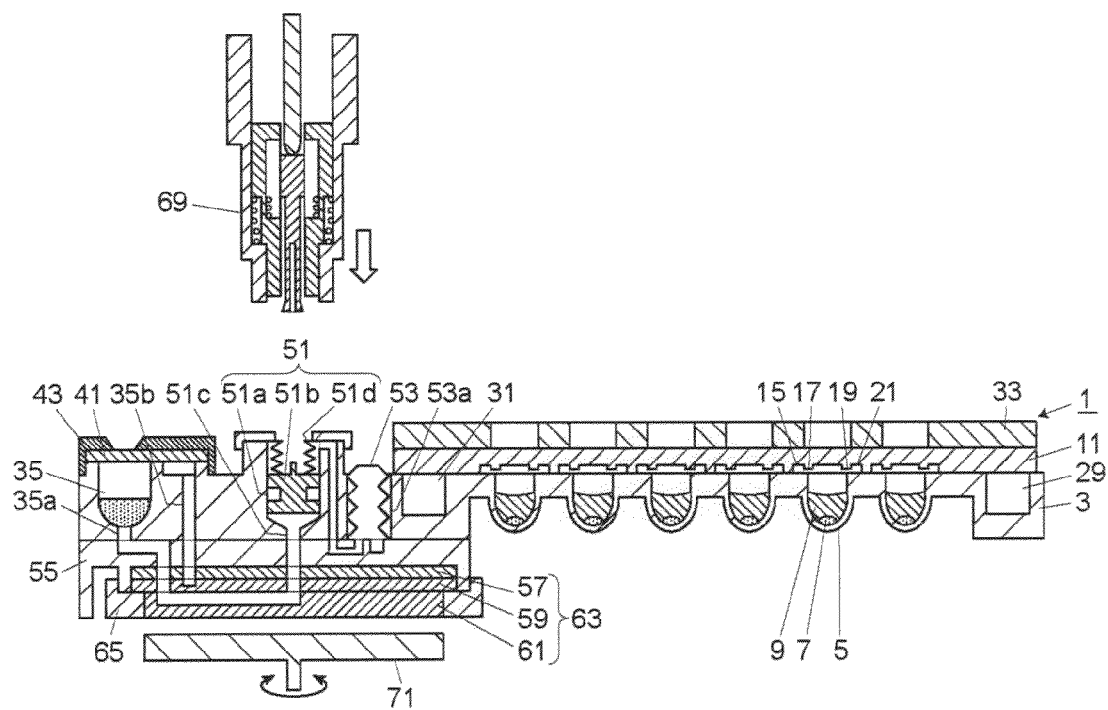
FIG. 7 is a schematic sectional view of the reactor plate and a reaction processing apparatus for processing the reactor plate.

FIG. 7 is a sectional view showing a reaction processing apparatus for processing the reactor plate 1 shown in FIGS. 1A, 1B and 1C as well as the reactor plate 1. The reactor plate 1 shown in FIG. 7 has the same structure as that shown in FIGS. 1A, 1B and 1C and, therefore, the description thereof is omitted.

The reaction processing apparatus includes a temperature control system for controlling the temperature of the reaction wells 5, a syringe driving unit 69 for driving the syringe 51, and a switching valve driving unit 71 for switching the switching valve 63.

FIGS. 8 to 14 are plan views for explaining the operation of introducing a sample liquid into the reaction wells 5 from the sample well 35. This operation will be described with reference to FIGS. 1A-1C and 8 to 14.

A dispensing device having a sharp tip (not shown) is prepared, and the dispensing device is passed through the septum 41 provided on the sample well 35 to dispense, for example, 5 μL of a sample liquid into the sample well 35. After the completion of the dispensing of the sample liquid, the dispensing device is pulled out of the septum 41. By pulling the dispensing device out of the septum 41, a through hole formed in the septum 41 is closed due to the elasticity of the septum 41.

The syringe driving unit 69 is connected to the plunger 51b of the syringe 51, and the switching valve driving unit 71 is connected to the switching valve 63.

Figure 8:
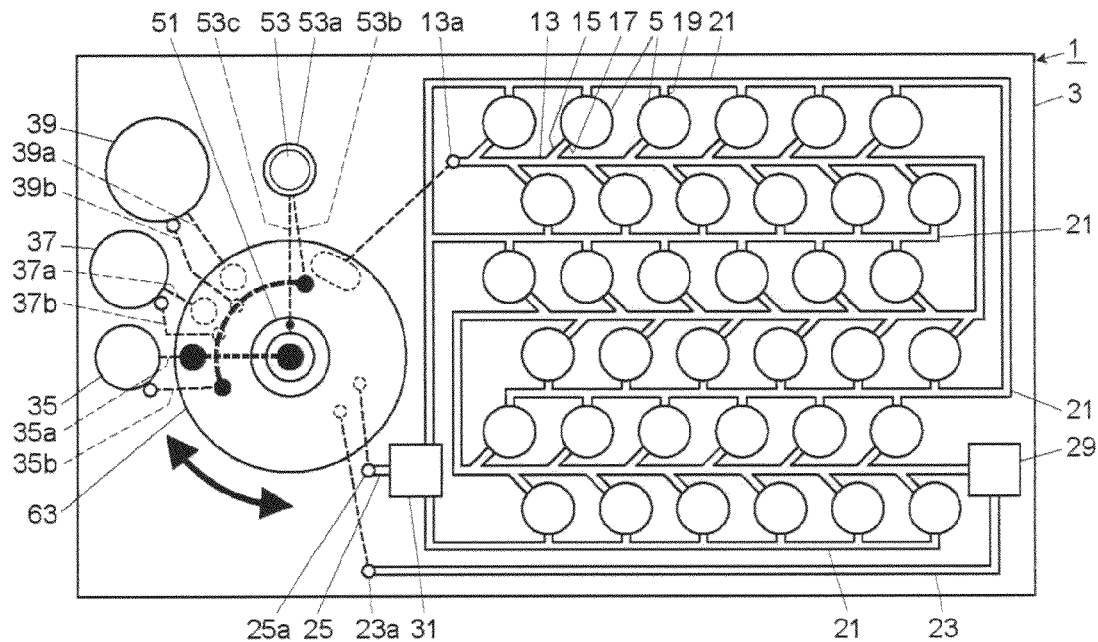
FIG. 8 is a plan view for explaining the operation of introducing a sample liquid into reaction wells from a sample well.

As shown in FIG. 8, the switching valve 63 in its initial state shown in FIG. 1A is rotated to connect the syringe channel 51c to the sample channel 35a and to connect the air vent channel 53b to the sample well air vent channel 35b. At this time, the air vent channels 37b and 39b are also connected to the air vent channel 53b. The sample well 35 contains, for example, 45 μL of a reagent 45.

The plunger 51b of the syringe 51 is allowed to slide to mix the sample liquid and the reagent 45 contained in the sample well 35. Then, for example, only 10 μL of the liquid mixture contained in the sample well 35 is sucked into the channel in the switching valve 63, the syringe channel 51c, and the syringe 51. At this time, the bellows 53 expands and contracts with changes in the volume of a gas contained in the sample well 35 because the sample well 35 is connected the bellows 53 through the air vent channels 35e, 35d, and 35b, the switching valve 63, and the air vent channel 53b. Further, the cover body 51d is deformed by sliding the plunger 51b so that the internal capacity of the sealed space 51e (see FIG. 1C) is changed. The bellows 53 expands and contracts also with changes in the internal capacity of the sealed space 51e because the sealed space 51e is connected to the bellows 53 through the syringe air vent channel 53c. Also in the operation steps which will be described below, the bellows 53 expands and contracts with changes in the internal capacity of the sealed space 51e due to the sliding of the plunger 51b.

Figure 9:
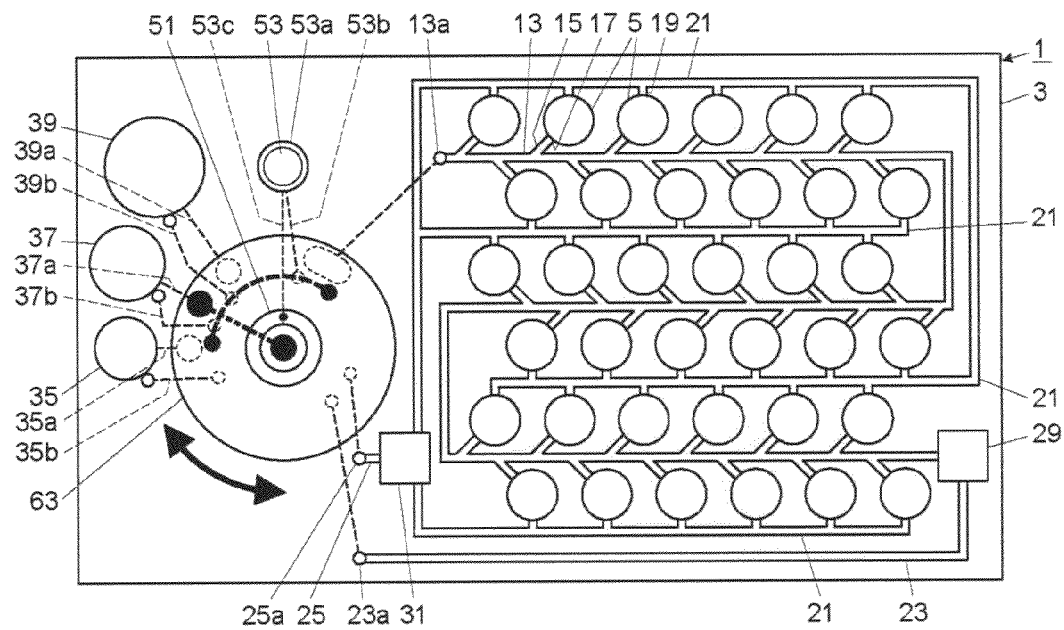
FIG. 9 is a plan view for explaining operation following the operation explained with reference to FIG. 8.

As shown in FIG. 9, the switching valve 63 is rotated to connect the syringe channel 51c to the reagent channel 37a and to connect the air vent channel 53b to the reagent well air vent channel 37b. The reagent well 37 contains, for example, 190 μL of dilution water 49. The mixture sucked into the channel in the switching valve 63, the syringe channel 51c, and the syringe 51 is injected into the reagent well 37. Then, the syringe 51 is slidably moved to mix the mixture and the dilution water 49. For example, the whole diluted mixture, that is, 200 μL of the diluted mixture is sucked into the channel in the switching valve 63, the syringe channel 51c, and the syringe 51. At this time, the bellows 53 expands and contracts with changes in the volume of a gas contained in the reagent well 37, since the reagent well 37 is connected to the bellows 53 through the air drain channels 37e, 37d, and 37b, the switching valve 63, and the air vent channel 53b.

Figure 10:
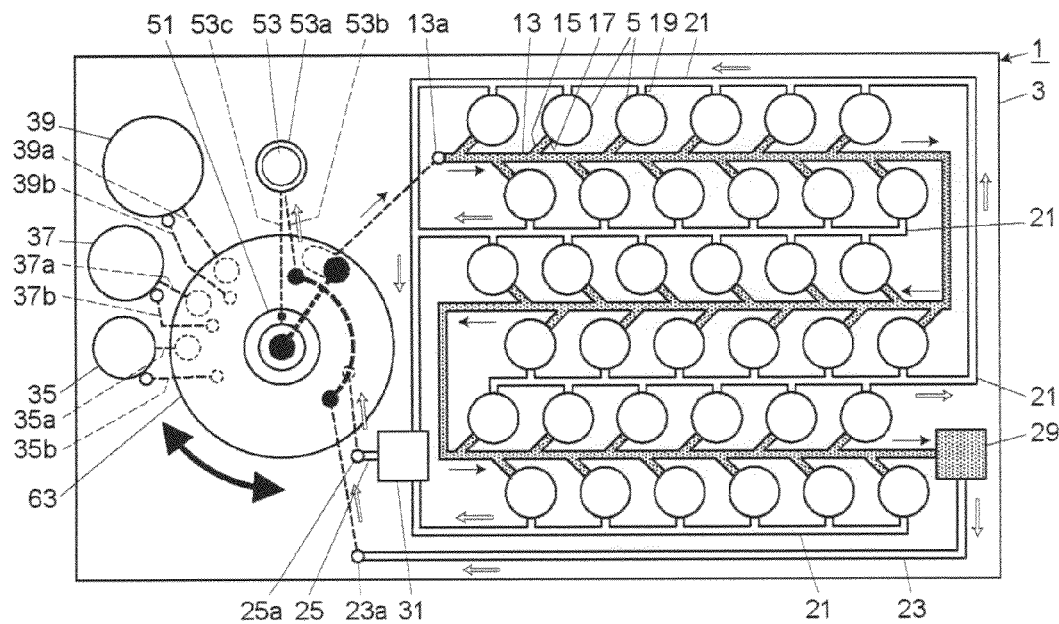
FIG. 10 is a plan view for explaining operation following the operation explained with reference to FIG. 9.

As shown in FIG. 10, the switching valve 63 is rotated to connect the syringe channel 51c to the channel 13a connected to one end of the main channel 13 and to connect the air vent channel 53b to the channels 23a and 25a connected to the liquid drain space 29 and the air drain space 31, respectively. The syringe 51 is driven in an extrusion direction to send the diluted mixture sucked into the channel in the switching valve 63, the syringe channel 51c, and the syringe 51 to the main channel 13. As shown by the arrows and dots in FIG. 10, the diluted mixture injected into the main channel 13 through the channel 13a fills the metering channels 15 one after another in order of increasing distance from the channel 13a, and then reaches the liquid drain space 29. The injection channel 17 allows the passage of a gas but does not allow the passage of the diluted mixture at an introduction pressure applied to introduce the diluted mixture into the main channel 13 and the metering channels 15. When the diluted mixture is introduced into the metering channel 15, a gas contained in the metering channel 15 is transferred into the reaction well 5 through the injection channel 17. Due to the transfer of the gas into the reaction well 5, a gas contained in the reaction well 5 is partially transferred into the reaction well air vent channels 19 and 21. Furthermore, a gas contained in the channels between the reaction well air vent channel 19 and the bellows 53 is sequentially moved toward the bellows 53 (see open arrows in FIG. 10). Further, due to the injection of the diluted mixture into the liquid drain space 29, a gas contained in the channels between the liquid drain space 29 and the bellows 53 is sequentially moved toward the bellows 53 (see open arrows in FIG. 10). As a result, the bellows 53 expands.

Figure 11:
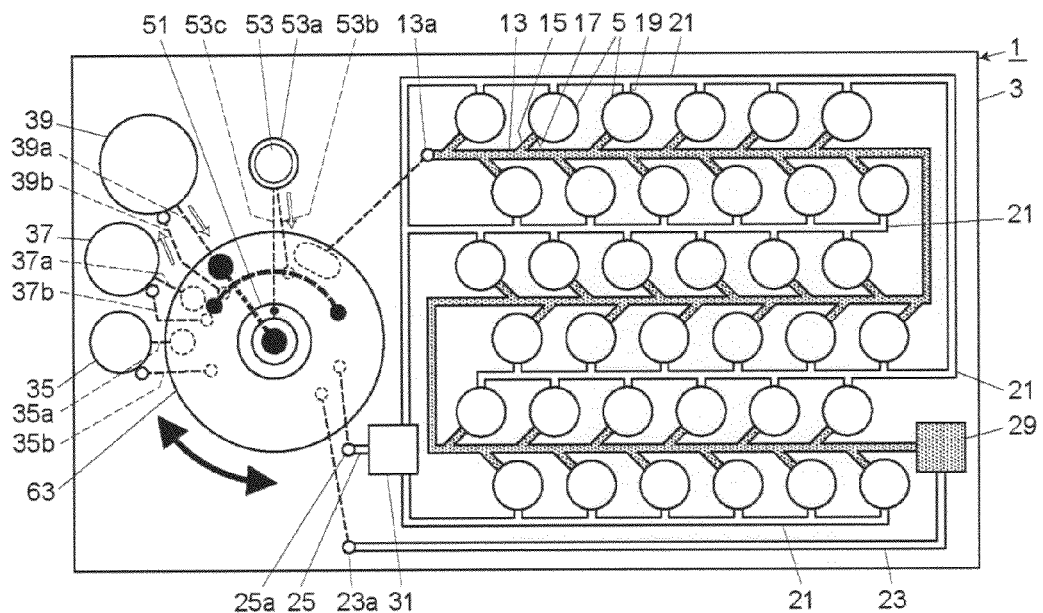
FIG. 11 is a plan view for explaining operation following the operation explained with reference to FIG. 10.

As shown in FIG. 11, the switching valve 63 is rotated to connect the syringe channel 51c to the channel 39a for air suction and to connect the air vent channel 53b to the air vent channel 39b for the well for air suction. Then, the syringe 51 is driven in a suction direction to suck a gas contained in the well 39 for air suction into the channel in the switching valve 63, the syringe channel 51c, and the syringe 51. At this time, the bellows 53 contracts due to the decompression of the well 39 for air suction (see open arrows in FIG. 11), since the well 39 for air suction is connected to the bellows 53 through the air vent channels 39e, 39d, and 39b, the switching valve 63, and the air vent channel 53b.

Figure 12:
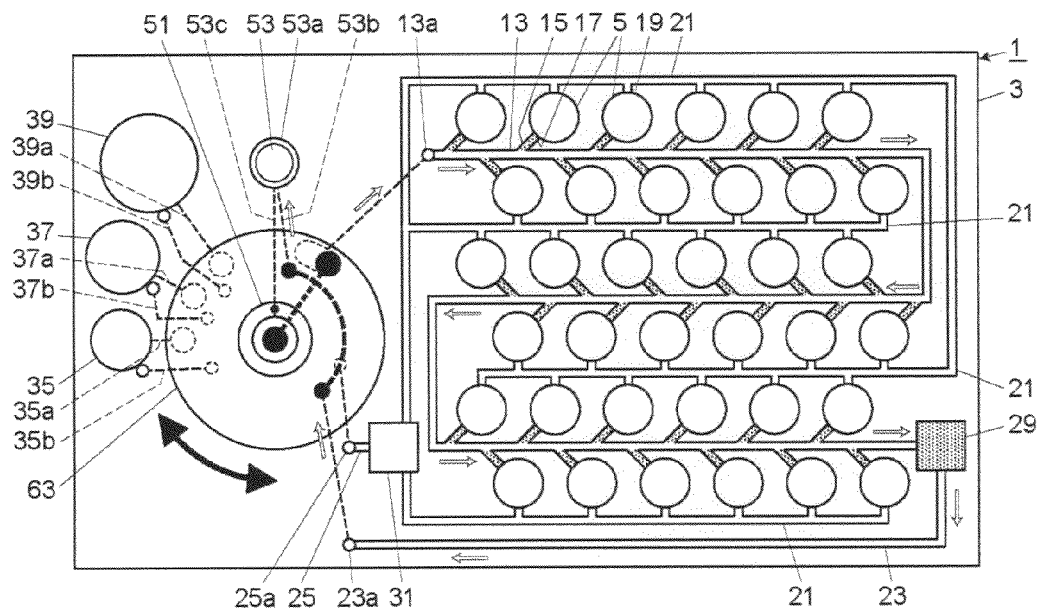
FIG. 12 is a plan view for explaining operation following the operation explained with reference to FIG. 11.

As shown in FIG. 12, the switching valve 63 is rotated to connect the syringe channel 51c to the channel 13a and to connect the air vent channel 53b to the channels 23a and 25a as in the case of a connection state shown in FIG. 10. Then, the syringe 51 is driven in an extrusion direction to send a gas contained in the channel in the switching valve 63, the syringe channel 51c, and the syringe 51 into the main channel 13 to purge the diluted mixture from the main channel 13 (see open arrows in FIG. 12). At this time, the diluted mixture remains in the metering channels 15 (see dots in FIG. 12) because the injection channels 17 do not allow the passage of the diluted mixture at a purge pressure applied to purge the diluted mixture from the main channel 13. The purged diluted mixture is injected into the liquid drain space 29. Further, due to the injection of the diluted mixture into the liquid drain space 29, a gas contained in the channels between the liquid drain space 29 and the bellows 53 is sequentially moved toward the bellows 53 (see open arrows in FIG. 12). As a result, the bellows 53 expands.

Figure 13:
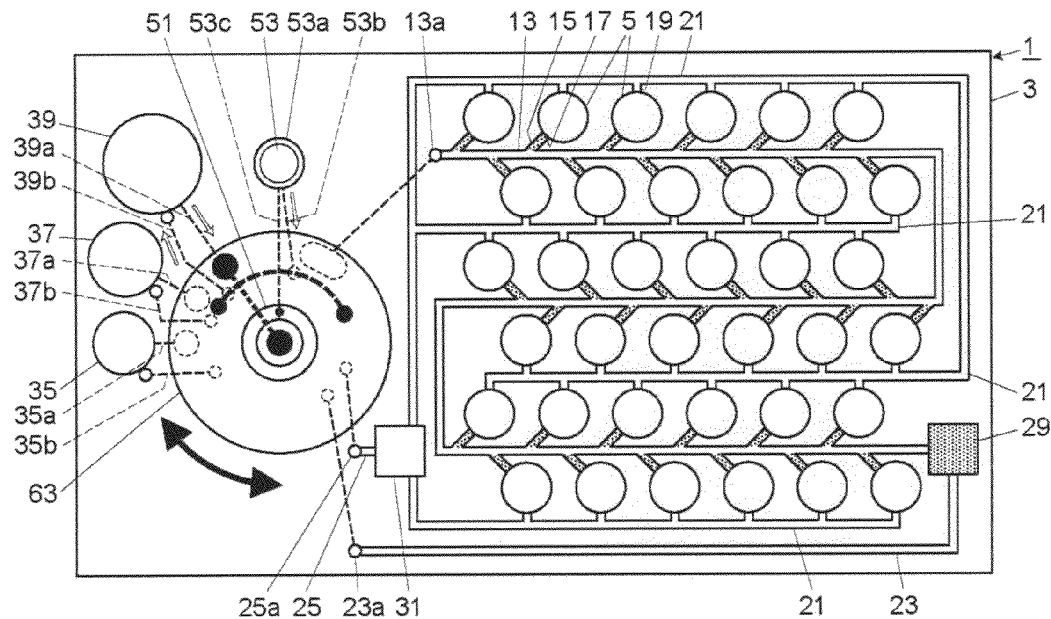
FIG. 13 is a plan view for explaining operation following the operation explained with reference to FIG. 12.

As shown in FIG. 13, the switching valve 63 is rotated to connect the syringe channel 51c to the channel 39a for air suction and to connect the air vent channel 53b to the air vent channel 39b for the well for air suction as in the case of a connection state shown in FIG. 11. Then, the syringe 51 is driven in a suction direction to suck a gas contained in the well 39 for air suction into the channel in the switching valve 63, the syringe channel 51c, and the syringe 51. At this time, as in the case described with reference to FIG. 11, the bellows 53 contracts (see open arrows in FIG. 13).

Figure 14:
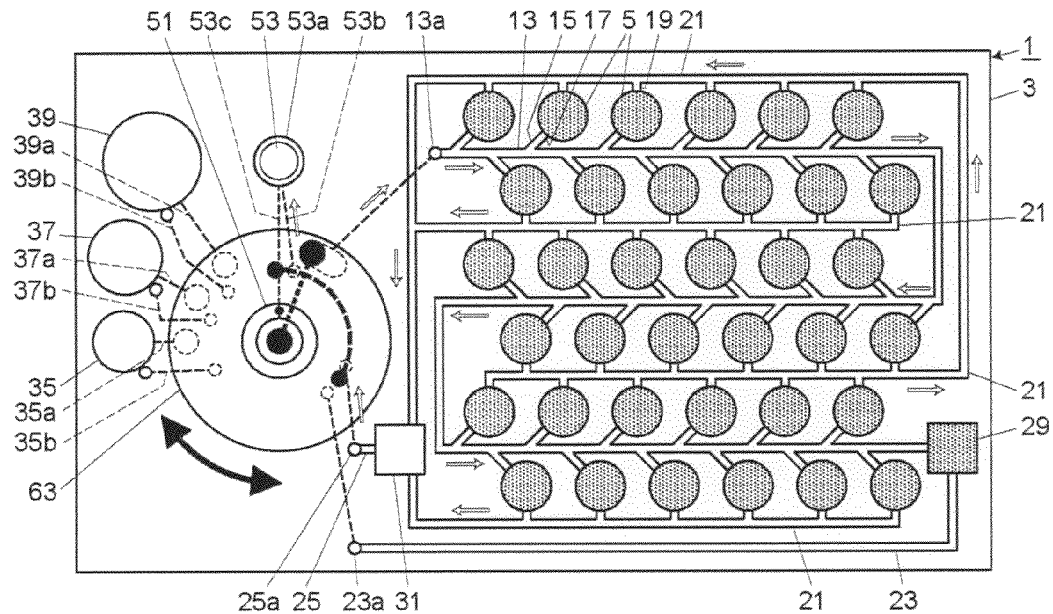
FIG. 14 is a plan view for explaining operation following the operation explained with reference to FIG. 13.

As shown in FIG. 14, the switching valve 63 is rotated to connect the syringe channel 51c to the channel 13a and to connect the air vent channel 53b to the channel 25a. It is noted that the connection state shown in FIG. 14 is different from those shown in FIGS. 10 and 12 in that the liquid drain space 29, to which the downstream end of the main channel 13 is connected, is not connected to the channel in the switching valve 63. Then, the syringe 51 is driven in an extrusion direction. Since the downstream end of the main channel 13 is not connected to the bellows 53, a pressure larger than the liquid introduction pressure and the purge pressure is applied to the inside of the main channel 13. As a result, the diluted mixture in the metering channels 15 is injected into the reaction wells 5 through the injection channels 17. After the completion of the injection of the diluted mixture into the reaction wells 5, a gas contained in the main channel 13 is partially flown into the reaction wells 5 through the metering channels 15 and the injection channels 17. At this time, a gas contained in the channels between the reaction wells 5 and the bellows 53 is sequentially moved toward the bellows 53 (see open arrows in FIG. 14), since the reaction wells 5 are connected to the bellows 53 through the reaction well air vent channels 19 and 21, the air drain space 31, the drain space air vent channel 25a, and the air vent channel 53b. As a result, the bellows 53 expands.

The switching valve 63 is returned to its initial state shown in FIG. 1A to hermetically seal the wells, channels, and drain spaces provided in the reactor plate 1. Then, the reaction wells 5 are heated by the temperature control system 67 to melt the wax 9. As a result, the diluted mixture injected into each of the reaction wells 5 sinks below the wax 9 and, therefore, the diluted mixture is mixed with the reagent 7 so that a reaction occurs. As described above, by using the reactor plate 1, it is possible to perform reaction processing in a closed system.

Alternatively, the wax 9 may be melted before the injection of the diluted mixture into the reaction wells 5 by heating the reaction wells 5 by the temperature control system 67 so that the diluted mixture is injected into the reaction wells 5 containing the melted wax 9. In this case, the diluted mixture injected into each of the reaction wells 5 immediately sinks below the wax 9, and is then mixed with the reagent 7 so that a reaction occurs. Even when the switching valve 63 is in the connection state shown in FIG. 14, the hermeticity of the reactor plate 1 is maintained by the bellows 53. By returning the switching valve 63 to its initial state shown in FIG. 1A after the injection of the diluted mixture into the reaction wells 5, it is possible to hermetically seal the wells, channels, and the drain spaces provided in the reactor plate 1. It is noted that the switching valve 63 may be returned to its initial state shown in FIG. 1A at any timing during the period from just after the injection of the diluted mixture into the reaction wells 5 until the end of the reaction between the diluted mixture and the reagent 7, or may be returned to its initial state shown in FIG. 1A after the completion of the reaction between the diluted mixture and the reagent 7.

As described above, by using the reactor plate 1, it is possible to perform reaction processing in a closed system. In addition, it is also possible to maintain the hermeticity of the reactor plate 1 before and after reaction processing.

According to the present embodiment, grooves for forming the channels 13, 15, 17, 19, 21, and 23 are provided in the channel base 11, but the present invention is not limited to this embodiment. For example, grooves for forming all or part of these channels may be provided in the surface of the well base 3.

Figure 15:
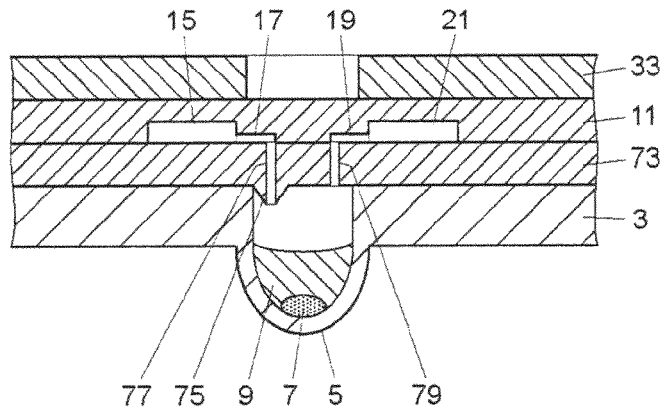
FIG. 15 is a schematic expanded sectional view of a reaction well of a reactor plate according to another embodiment of the present invention and its vicinity.

FIG. 15 is an expanded sectional view schematically showing a reaction well of a reactor plate according to another embodiment of the present invention and its vicinity. The reactor plate according to another embodiment of the present invention has the same structure as the reactor plate described above with reference to FIGS. 1A to 14 except that a channel spacer is provided between the well base and the channel base.

On the well base 3, a channel spacer 73 is provided to cover a region where the reaction wells 5 are arranged. On the channel spacer 73, the channel base 11 and the channel cover 33 are further provided in this order. The channel spacer 73 is made of, for example, PDMS or silicone rubber. The thickness of the channel spacer 73 is, for example, from 0.5 to 5.0 mm. The channel spacer 73 has a projecting portion 75 projecting into each of the reaction wells 5. The projecting portion 75 is substantially trapezoidal in cross section. For example, the proximal end of the projecting portion 75 has a width of 1.0 to 2.8 mm, and the distal end of the projecting portion 75 has a width of 0.2 to 0.5 mm. That is, the distal end of the projecting portion 75 is narrower than the proximal end of the projecting portion 75. Further, the projecting portion 75 has a super-water-repellent surface. In this regard, it is noted that it is not always necessary to subject the surface of the projecting portion 75 to water-repellent treatment.

Further, in the channel spacer 73, an injection channel 77 is provided at a position corresponding to each of the projecting portions 75. The injection channel 77 is constituted from a through hole extending from the distal end of the projecting portion 75 to the surface of the channel spacer 73 where the projecting portion 75 is not provided. The injection channel 77 has an inner diameter of, for example, 500 μm. The opening of the injection channel 77 provided on the channel base 11 side is connected to the injection channel 17 provided in the channel base 11. It is noted that the reactor plate according to another embodiment of the present invention is different from the reactor plate described above with reference to FIGS. 1A to 14 in that the channel base 11 does not have a recess 27.

Further the channel spacer 73 has a reaction well air vent channel 79 constituted from a through hole. The reaction well air vent channel 79 is provided to allow the reaction well 5 to communicate with the reaction well air vent channel 19 provided in the channel base 11.

Although not shown in FIG. 15, the channel spacer 73 has through holes at positions corresponding to both ends of the main channel 13, one end of each of the reaction well air vent channels 21 located on the air drain space 31 side, and both ends of each of the drain space air vent channels 23 and 25 to connect these channels 13, 21, 23, and 25 to the wells 29 and 31 provided in the well base 3 and the channels 23a and 25a.

According to the embodiment of the present invention shown in FIG. 15, the end of the injection channel 77 on the opposite side from the injection channel 17 (i.e., the other end of the injection channel) is located at the tip of the projecting portion 75 which projects from the top inner surface of the reaction well 5 and, therefore, a liquid is easily dropped into the reaction well 5 through the injection channels 17 and 77 when injected into the reaction well 5.

Further, by placing the tip of the projecting portion 75 in the vicinity of the side wall of the reaction well 5 so that when a liquid passes through the injection channel 77 and is then discharged from the tip of the projecting portion 75, a droplet of the liquid formed at the tip of the projecting portion 75 can come into contact with the side wall of the reaction well 5, it is possible to inject the liquid into the reaction well 5 along the side wall of the reaction well 5, thereby making it possible to more reliably inject the liquid into the reaction well 5. However, the projecting portion 75 may be provided at a position which does not allow a droplet formed at the tip of the projecting portion 75 to be brought into contact with the side wall of the reaction well 5.

Figure 16:
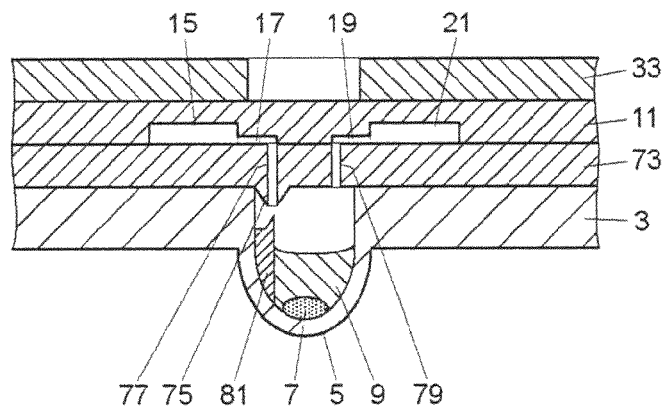
FIG. 16 is a schematic expanded sectional view of a reaction well of a reactor plate according to another embodiment of the present invention and its vicinity.

FIG. 16 is an expanded sectional view schematically showing a reaction well of a reactor plate according to another embodiment of the present invention and its vicinity.

The reactor plate according to another embodiment of the present invention shown in FIG. 16 is different from the reactor plate described above with reference to FIG. 15 in that a projecting portion 81 is further provided in the reaction well 5. The tip of the projecting portion 81 is located under the tip of the projecting portion 75. By providing the projecting portion 81, it becomes easy to guide a droplet formed at the tip of the projecting portion 75 into the reaction well 5. The projecting portion 81 becomes particularly effective by subjecting the surface of at least the tip of the projecting portion 81 to hydrophilic treatment.

Figure 17:
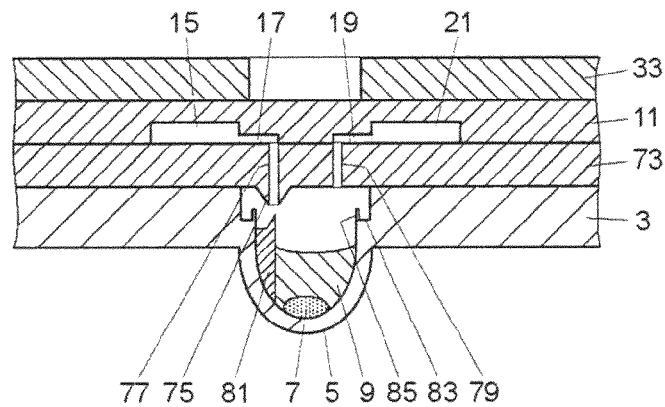
FIG. 17 is a schematic expanded sectional view of a reaction well of a reactor plate according to another embodiment of the present invention and its vicinity.

FIG. 17 is an expanded sectional view schematically showing a reaction well of a reactor plate according to another embodiment of the present invention and its vicinity.

The reactor plate according to another embodiment of the present invention shown in FIG. 17 is different from the reactor plate described above with reference to FIG. 16 in that a stepped portion 83 and a linear projecting portion 85, which is provided on the top surface of the stepped portion 83 in such a manner that a space is left between the tip of the linear projecting portion 85 and the top surface of the reaction well 5, is further provided in the side wall of the reaction well 5. The stepped portion 83 and the linear projecting portion 85 are circular when viewed from above. The tip of the linear projecting portion 85 is provided in such a manner that a space is left between the tip of the linear projecting portion 85 and the side wall of the reaction well 5.

By providing the linear projecting portion 85 in such a manner that a space is left between the tip of the linear projecting portion 85 and the top surface of the reaction well 5 and between the tip of the linear projecting portion 85 and the side wall of the reaction well 5, it is possible to prevent a liquid contained in the reaction well 5 from reaching the top surface of the reaction well 5 through the side wall of the reaction well 5. The linear projecting portion 85 becomes particularly effective by subjecting the surface of at least the tip of the linear projecting portion 85 to water-repellent treatment.

The stepped portion 83 and the linear projecting portion 85 shown in FIG. 17 can also be applied to the embodiment shown in FIG. 15.

In each of these various embodiments described above with reference to FIGS. 15 to 18, grooves for forming the channels 13, 15, 17, 19, 21, and 23 are provided in the channel base 11, but the present invention is not limited to these embodiments. For example, grooves for forming all or part of these channels may be provided in any one of the surfaces of the channel spacer 73 located on the channel base 11 side, the surface of the channel spacer 73 located on the well base 3 side, and the surface of the well base 3.

A part of the cylinder 51a of the syringe 51 may be constituted from a part of the switching valve 63.

Figure 18A:
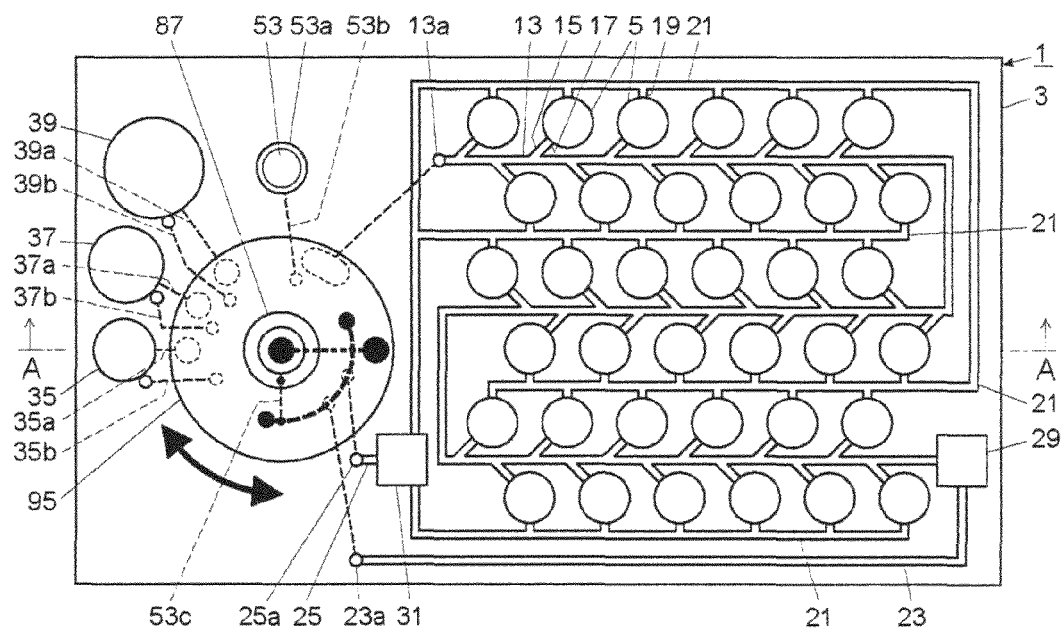
FIG. 18A is a schematic plan view of a reactor plate according to another embodiment of the present invention.
Figure 18B:
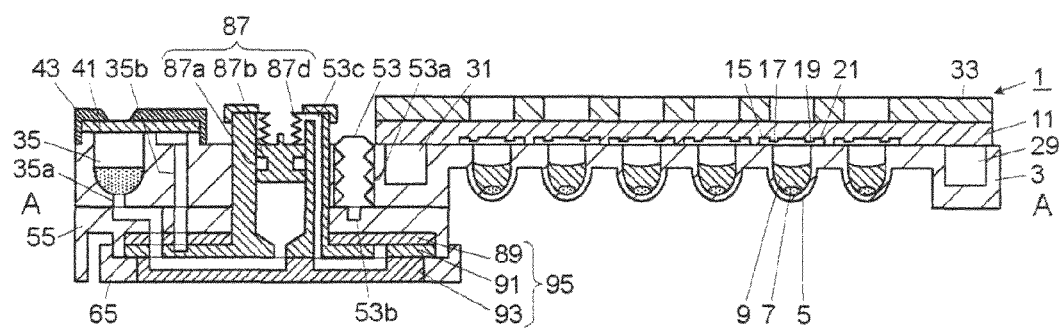
FIG. 18B is a schematic sectional view taken along the A-A line in FIG. 18A, which further includes the sectional views of a metering channel 15, an injection channel 17, reaction well air vent channels 19 and 21, a liquid drain space 29, an air drain space 31, and a bellows 53.
Figure 18C:
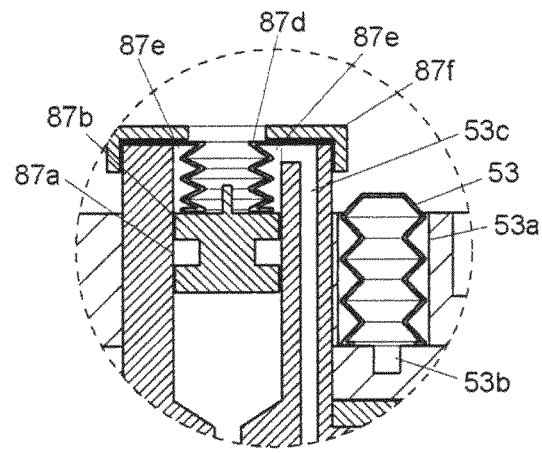
FIG. 18C is a schematic expanded sectional view of a syringe 51 and the bellows 53 of the reactor plate in the embodiment shown in FIG. 18A and their vicinity.
Figure 19A:
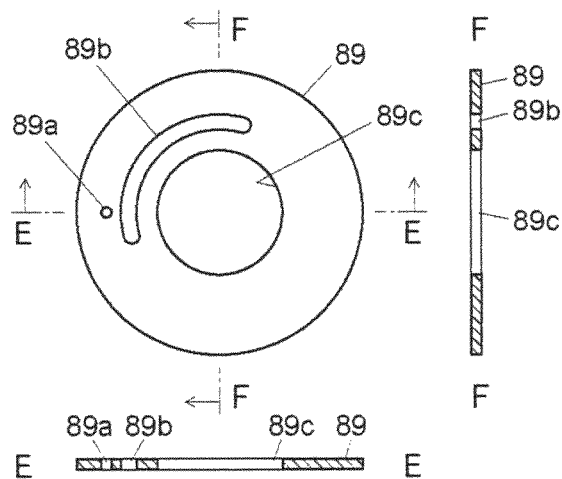
FIG. 19A shows a schematic plan view and schematic sectional views of a sealing plate of a switching valve of the reactor plate in the embodiment shown in FIG. 18A.
Figure 19B:
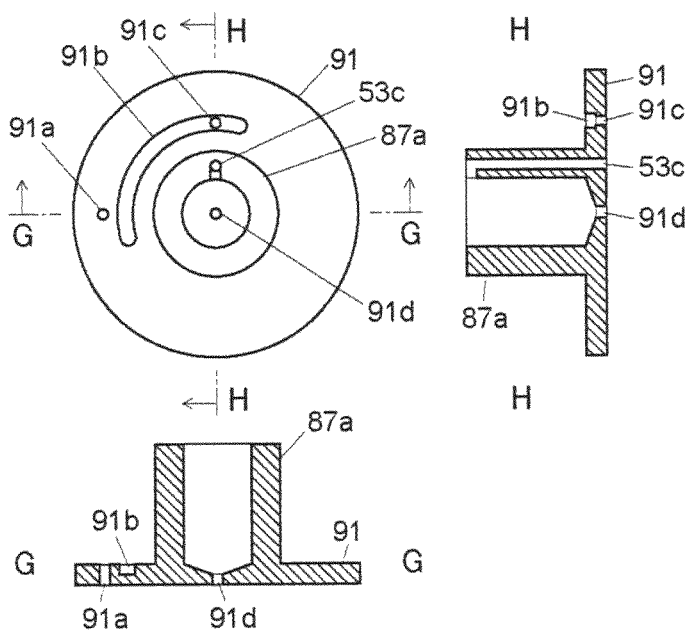
FIG. 19B shows a schematic plan view and schematic sectional views of a rotor upper of the switching valve of the reactor plate in the embodiment shown in FIG. 18A.
Figure 19C:
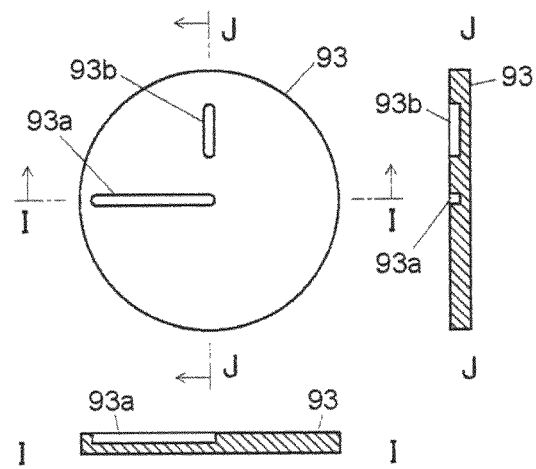
FIG. 19C shows a schematic plan view and schematic sectional views of a rotor base of the switching valve of the reactor plate in the embodiment shown in FIG. 18A.

FIGS. 18A, 18B, and 18C show a reactor plate according to another embodiment of the present invention. More specifically, FIG. 18A is a schematic plan view of the reactor plate according to another embodiment of the present invention, FIG. 18B is a schematic sectional view taken along the A-A line in FIG. 18A, which further includes the sectional views of the metering channel 15, the injection channel 17, the reaction well air vent channels 19 and 21, the liquid drain space 29, the air drain space 31, and the bellows 53, and FIG. 18C is an expanded sectional view schematically showing a syringe 51, the bellows 53 and their vicinity. FIGS. 19A, 19B, and 19C are schematic exploded views of a switching valve 95. More specifically, FIG. 19A shows a plan view and sectional views of a sealing plate 89, FIG. 19B shows a plan view and sectional views of a rotor upper 91, and FIG. 19C shows a plan view and sectional views of a rotor base.

In the reactor plate in the embodiment shown in FIG. 18A, the syringe 87 has a cylinder 87a made of, for example, a resin material such as polypropylene or polycarbonate, and the cylinder 87a is integrally molded with the rotor upper 91 of the switching valve 95.

The syringe 87 is constituted from the cylinder 87a provided in a through hole formed in the well base 3 and the well bottom 55, a plunger 87b placed in the cylinder 87a, and a cover body 87d.

The cover body 87d has flexibility in the sliding direction of the plunger 87b, and is connected to the cylinder 87a and the plunger 87b. The cover body 87d is provided to create a sealed space 87e to hermetically cut off a part of an inner wall of the cylinder 87a to be brought into contact with the plunger 87b from an atmosphere outside the cylinder 87a. The sealed space 87e is enclosed with the cylinder 87a, the plunger 87b, and the cover body 87d.

One end of the cover body 87d connected to the cylinder 87a is hermetically fixed to the upper end of the cylinder 87a by a cylinder cap 87f. On the other hand, the other end of the cover body 87d connected to the plunger 87b is hermetically connected to the upper surface of the plunger 87b by an adhesive. However, a method for connecting the cover body 87d to the cylinder 87a and the plunger 87b is not limited to the method described above, and the connecting positions of the cover body 87d are not limited to those described above. The plunger and the cover body may be integrally molded. The plunger and the cover body can be integrally molded using, for example, silicone rubber.

As described above, the cover body 87d is connected to the cylinder 87a and the plunger 87b to create a sealed space 87e enclosed with the cylinder 87a, the plunger 87b, and the cover body 87d and, therefore, it is possible to prevent the entry of foreign matter from outside through a gap between the cylinder 87a and the plunger 87b. In addition, it is also possible to prevent the leakage of a liquid through the gap between the cylinder 87a and the plunger 87b, thereby preventing the pollution of an outside environment with the liquid. It is to be noted that as described above, since the cover body 87d has flexibility in the sliding direction of the plunger 87b, the plunger 87b can be slidably moved.

Referring to FIGS. 19A, 19B, and 19C, the syringe air vent channel 53c and the switching valve 95 will be described.

The switching valve 95 is constituted from the disk-shaped sealing plate 89, rotor upper 91, and rotor base 93, and is attached to the well bottom 55 by means of a lock 65.

The sealing plate 89 has a through hole 89a, a through groove 89b, and a through hole 89c. The through hole 89a is provided in the vicinity of the peripheral portion of the sealing plate 89, and is connected to any one of the channels 13a, 35a, 37a, and 39a. The through groove 89b is provided inside the through hole 89*a* and on a circle concentric with the sealing plate 89, and is connected to at least two of the channels 23*a*, 25*a*, 35*b*, 37*b*, 39*b*, and 53*b*. The through hole 89*c* is provided at the center of the sealing plate 89 to insert the cylinder 87*a* thereinto. On the surface of the sealing plate 89 opposed to the well bottom 55, a fluorine resin layer (not shown) is provided.

The rotor upper 91 has the cylindrical cylinder 87*a*, a through hole 91*a*, a groove 91*b*, a through hole 91*c*, and a through hole 91*d*. The cylinder 87*a* is provided on one surface of the rotor upper 91 so as to be located in the central portion of the rotor upper 91. The through hole 91*a* is provided at a position corresponding to the position of the through hole 89*a* provided in the sealing plate 89. The groove 91*b* is provided in the surface of the rotor upper 91 so as to correspond to the through groove 89*b* provided in the sealing plate 89. The through hole 91*c* is provided in the groove 91*b*, and the through hole 91*d* is provided at the center of the rotor upper 91. The through hole 91*d* is located at the bottom of the cylinder 87*a* and constitutes a discharge port of the cylinder 87*a*.

In the rotor upper 91, the syringe air vent channel 53*c* constituted from a through hole extending from the upper end surface of the cylinder 87*a* to the back surface of the rotor upper 91 is also provided. In the upper end surface of the cylinder 87*a*, a notch extending from the surface of the inner wall of the cylinder 87*a* to the syringe air vent channel 53*c* is provided. As shown in FIG. 18C, the notch allows the sealed space 87*e* to communicate with the syringe air vent channel 53*c* in a state where the upper end surface of the cylinder 87*a* is covered with the cover body 87*d*.

The rotor base 93 has a groove 93*a* and a groove 93*b* in its surface to be bonded to the back surface of the rotor upper 91. The groove 93*a* is provided to connect the through hole 91*a* and the through hole 91*d* provided in the rotor upper 91 to each other, and the groove 93*b* is provided to connect the syringe air vent channel 53*c* and the through hole 91*c* provided in the rotor upper 91 to each other.

As shown in FIG. 18B, the sealing plate 89, the rotor upper 91, and the rotor base 93 constituting the switching valve 95 are superposed so that the cylinder 87*a* is inserted into the through hole 89*c* of the sealing plate 89.

The through hole 91*d* of the rotor upper 91 constituting a discharge port of the cylinder 87*a* is connected to the through hole 89*a* of the sealing plate 89 through the groove 93*a* of the rotor base 93 and the through hole 91*a* of the rotor upper 91.

The sealed space 87*e* (see FIG. 18C) is connected to the through groove 89*b* of the sealing plate 89 through the syringe air vent channel 53*c*, the groove 93*b* of the rotor base 93, the through hole 91*c* and the through groove 91*b* of the rotor upper 91.

Referring to FIGS. 18A, 18B, 18C, 19A, 19B, and 19C, channel connection will be described.

By rotating the switching valve 95, the through hole 91*d* of the rotor upper 91 constituting a discharge port of the cylinder 87*a* is connected to any one of the channels 13*a*, 35*a*, 37*a*, and 39*a* through the groove 93*a*, the through hole 91*a*, and the through hole 89*a*.

Further, at the same time as the through hole 91*d* is connected to any one of the channels 13*a*, 35*a*, 37*a*, and 39*a*, the air vent channel 53*b* is connected to at least any one of the channels 23*a*, 25*a*, 35*b*, 37*b*, and 39*b* through the through grooves 89*b* and 91*b*. At this time, the sealed space 87*e* is connected to the air vent channel 53*b* through the cylinder air vent channel 53*c*, the groove 93*b*, the through hole 91*c*, and the through grooves 89*b* and 91*b*.

According to this embodiment, it is possible to eliminate the necessity to provide a channel between the syringe 87 and the switching valve 95, thereby simplifying the channel configuration of the reactor plate.

In general, in a case where a channel has a joint, there is a possibility that a liquid or a gas will leak through the joint or a liquid will be accumulated in the joint. However, according to this embodiment, since the cylinder 87*a* and the rotor upper 91 are integrally molded, there is no joint between the syringe 87 and the switching valve 95 and, therefore, liquid leakage, gas leakage, and liquid accumulation do not occur between the syringe 87 and the switching valve 95.

In general, in a case where liquid accumulation occurs in the joint of a channel, there is a fear of reduction in the volume of a liquid to be fed through the channel, carry-over of a liquid accumulated in the joint of the channel into another liquid fed through the channel or a contamination of another liquid fed through the channel with a liquid accumulated in the joint of the channel, or fluctuation in the concentration of a liquid fed through the channel. However, according to this embodiment, since there is no joint between the syringe 87 and the switching valve 95, such a fear can be eliminated.

As shown in FIGS. 1A, 1B, and 1C, in a case where the channel 51*c* is provided between the syringe 51 and the switching valve 63 to arrange the syringe above the switching valve, the cylinder 51*a* cannot be formed in a portion where the channel 51*c* is provided. However, since the reactor plate according to the embodiment shown in FIGS. 18A, 18B, and 18C does not need to have a channel between the syringe 87 and the switching valve 95, the capacity of the cylinder 87*a* can be made larger than that of the cylinder 51*a* even when the cylinder 51*a* and the cylinder 81*a* have the same two-dimensional size.

In a case where the cylinder 87*a* is formed to have the same capacity and two-dimensional size as the cylinder 51*a*, the level of the upper end surface of the cylinder 87*a* can be made lower than that of the cylinder 51*a*. On the other hand, in a case where the cylinder 87*a* is formed to have the same capacity and the upper end surface level as the cylinder 51*a*, the two-dimensional size of the cylinder 87*a* can be made smaller than that of the cylinder 51*a*.

For example, even in a case where the upper end surface of the cylinder 51*a* needs to be located at a higher level than the upper surface of the entire reactor plate 1 due to limitations on the two-dimensional size of the entire reactor plate 1, since the level of the upper end surface of the cylinder 87*a* can be made lower than that of the cylinder 51*a* while the capacity and two-dimensional size of the cylinder 87*a* remain the same as the cylinder 51*a*, it is possible to allow the upper end surface of the cylinder 87*a* to be located at the same or lower level than the upper surface of the entire reactor plate 1. This makes it possible to eliminate problems caused by the cylinder whose upper end surface is located at a higher level than the upper surface of the entire reactor plate, such as difficulty in stacking two or more reactor plates on top of each other for storage and increase in the size of a package of the reactor plate.

By making the two-dimensional size of the cylinder 87*a* smaller than that of the cylinder 51*a* while the capacity of the cylinder 87*a* remains the same as the cylinder 51*a*, it is also possible to reduce the two-dimensional size of the entire reactor plate 1.

Although the present invention has been described above with reference to the various embodiments, the present invention is not limited to these embodiments. The shape, material, position, number, and size of each component and the channel configuration of the reactor plate in the above description are merely examples, and various changes can be made without departing from the scope of the present invention defined in claims.

For example, the bellows 53 connected to the air vent channel 53b may have another structure as long as it is a variable capacity member whose internal capacity is passively variable. Examples of such a bellows 53 having another structure include a bag-shaped one made of a flexible material and a syringe-shaped one.

The reactor plate according to the present invention does not always need to have a variable capacity member such as a bellows 53. Further, in a case where a liquid such as a reagent is not previously contained in the well 35, 37, or 39, the air vent channel thereof does not always need to partially have the channel 35e, 37e, or 39e constituted from a narrow hole.

In each of the above embodiments, the air vent channels 35b, 37b, and 39b, which communicate with the wells 35, 37, and 39 provided as sealed wells, are connected to the air vent channel 53b through the switching valve 63, but may be directly connected to the outside of the reactor plate or a variable capacity part such as a bellows 53. Each of the wells 35, 37, and 39 may be sealed by using an openable and closable cap.

In each of the above embodiments, the well base 3 is constituted from one component, but may be constituted from two or more components.

The reagent contained in the reaction well 5 may be a dry reagent.

It is noted that the sample well 35 and the reaction well 5 do not always need to previously contain a reagent.

In each of the above embodiments, the reagent well 37 contains dilution water 49, but may contain a reagent instead of the dilution water 49.

The well base 3 may further have a gene amplification well for carrying out gene amplification reaction. For example, the empty reagent well 37 may be used as a gene amplification well.

By previously placing a reagent for gene amplification reaction in the reaction well 5, it is possible to carry out gene amplification reaction in the reaction well 5.

In a case where a liquid to be introduced into the main channel 13 contains a gene, a probe which reacts with the gene may be previously placed in the reaction well 5.

In each of the above embodiments, the syringe 51 is placed on the switching valve 63. However, the position of the syringe 51 is not limited to a position on the switching valve 63, and the syringe 51 may be placed at any position.

In each of the above embodiments, the rotary switching valve 63 is used as a switching valve. However, a switching valve for use in the reactor plate according to the present invention is not limited thereto, and various channel switching valves can be used. The reactor plate according to the present invention may have a plurality of switching valves.

In each of the above embodiments, a liquid filling the metering channel 15 is injected into the reaction well 5 through the injection channel 17 by applying a pressure to the inside of the main channel 13 after air purge, but the reaction processing method according to the present invention is not limited to such a method. For example, a liquid filling the metering channel 15 may be injected into the reaction well 5 through the injection channel 17 by creating a negative pressure in the reaction well air vent channel 21 and then in the reaction well 5. In this case, it is necessary to change the channel configuration of the reactor plate so that a negative pressure can be created in the reaction well air vent channel 21 by using the syringe 51. Alternatively, another syringe may be additionally prepared. In this case, a positive pressure is created in the main channel 13 and a negative pressure is created in the reaction well 5 to inject the liquid into the reaction well 5.

In each of the above embodiments, one main channel 13 is provided, and all the metering channels 15 are connected to the main channel 13. However, the channel configuration of the reactor plate according to the present invention is not limited thereto. For example, a plurality of main channels may be provided. In this case, one or more metering channels may be connected to each of the main channels.

In the reactor plate according to the present invention, the main channel can be hermetically sealed. In this regard, the main channel may be hermetically sealed by, for example, allowing both ends of the main channel to be openable and closable. The phrase "allowing both ends of the main channel to be openable and closable" includes a case where each end of the main channel is connected to another space, and the end of the space located on the opposite side from the main channel is openable and closable. In the case of each of the above embodiments, such 'another space' corresponds to, for example, the channel 13a, the liquid drain space 29, the drain space air vent channel 23, or the channel 23a.

In the reactor plate according to the present invention, the reaction well air vent channel can be hermetically sealed. In this regard, the reaction well air vent channel may be hermetically sealed by, for example, allowing the end of the reaction well air vent channel located on the opposite side from the reaction well to be openable and closable. The phrase "allowing the end of the reaction well air vent channel located on the opposite side from the reaction well to be openable and closable" includes a case where the end of the reaction well air vent channel located on the opposite side from the reaction well is connected to another space, and the end of the space located on the opposite side from the reaction well air vent channel is openable and closable. In the case of each of the above embodiments, such 'another space' corresponds to, for example, the air drain space 31, the drain space air vent channel 25, or the channel 25a.

In the case of such an aspect, a liquid is introduced into the main channel and the metering channels, and next, the liquid is purged from the main channel, and further, the liquid remaining in the metering channels is injected into the reaction wells, and thereafter both ends of the main channel and one end of the reaction well air vent channel located on the opposite side from the reaction well are closed to hermetically seal the main channel and the reaction well air vent channel.

The present invention can be applied to measurements of various chemical and biochemical reactions.

What is claimed is:
1. A reactor plate comprising:
a sealed reaction well;
a reaction well channel connected to the reaction well; and
a syringe for sending a liquid to the reaction well channel and the reaction well, wherein the syringe has a cylinder having a discharge port connected to the reaction well channel, a plunger placed in the cylinder, and a cover body for hermetically cutting off a part of an inner wall of the cylinder to be brought into contact with the plunger from an atmosphere outside the cylinder,
wherein the cover body has flexibility in the sliding direction of the plunger, and is connected to the cylinder and the plunger to create a sealed space enclosed with the cylinder, the plunger, and the cover body, wherein a first end of the cover body is hermetically fixed to an upper end of the cylinder, and a second end of the cover body is hermetically connected to an upper surface of the plunger, wherein edges of the upper surface of the plunger contact an inner surface of the cylinder, and the sealed space is arranged completely within the cylinder, and wherein the reactor plate further comprises:

a variable capacity part formed separately from the syringe and provided apart from the syringe, the variable capacity part having a sealed internal space with capacity being passively variable;

a syringe air vent channel provided between the syringe and the variable capacity part, the syringe air vent channel having one end connected to the sealed space and another end connected to the variable capacity part; and a reaction well air vent channel connected to the reaction well, the reaction well air vent channel being connected to the variable capacity part.

2. The reactor plate according to claim 1, further comprising a sealed well provided separately from the reaction well, a sealed well channel connected to the sealed well, and a switching valve for connecting the syringe to the reaction well channel or the sealed well channel.

3. The reactor plate according to claim 2, wherein the sealed well is a sample well for containing a sample liquid.

4. The reactor plate according to claim 3, wherein the sample well is sealed with an elastic member which allows a dispensing device having a sharp tip to pass through to form a through hole and which also allows the through hole to be closed by pulling out the dispensing device due to its elasticity.

5. The reactor plate according to claim 4, wherein the sample well contains a liquid for pretreating a sample or a reagent.

6. The reactor plate according to claim 2, further comprising one or more reagent wells, each of which is a sealed well, other than the sample well, wherein the reagent well contains a reagent to be used for the reaction of a sample liquid and is sealed with a film, or has an openable and closable cap so that the reagent can be injected thereinto.

7. The reactor plate according to claim 2, further comprising a gene amplification well which is a sealed well and is used for carrying out gene amplification reaction.

8. The reactor plate according to claim 2, wherein the switching valve is a rotary valve.

9. The reactor plate according to claim 8, wherein the rotary valve has a port to be connected to the syringe at the center of rotation and the syringe is placed on the rotary valve.

10. The reactor plate according to claim 1, wherein the reaction well channel is constituted from a groove formed in the contact surface between two members bonded together, or from the groove and a through hole formed in both or one of the members, and includes a main channel connected to the syringe, a metering channel branched off the main channel and having a predetermined capacity, and an injection channel whose one end is connected to the metering channel and whose other end is connected to the reaction well, and wherein the main channel and the reaction well air vent channel can be hermetically sealed, and the injection channel is formed narrower than the metering channel, and does not allow the passage of a liquid at a liquid introduction pressure applied to introduce the liquid into the main channel and the metering channel and at a purge pressure applied to purge the liquid from the main channel but allows the passage of the liquid at a pressure higher than the liquid introduction pressure and the purge pressure.

11. The reactor plate according to claim 10, wherein the contact angle of the injection channel with a water droplet is 90° or larger, and the area of an interface between the injection channel and the metering channel is 1 to 10,000,000 $\mu m^2$.

12. The reactor plate according to claim 10, which comprises a plurality of the reaction wells, wherein the metering channel and the injection channel are provided for each of the reaction wells and the plurality of metering channels are connected to the main channel.

13. The reactor plate according to claim 10, further comprising a projecting portion which projects from a top inner surface of the reaction well and has a proximal end and a distal end narrower than the proximal end, wherein the other end of the injection channel is located at the tip of the projecting portion.

14. The reactor plate according to claim 1, wherein the reaction well is made of an optically-transparent material so that optical measurement can be carried out from the bottom of the reaction well or from above the reaction well.

15. The reactor plate according to claim 1, wherein a liquid to be injected into the reaction well contains a gene, and the reaction well contains a probe which reacts with the gene.

16. A reaction processing method using the reactor plate according to claim 10, comprising:
filling the main channel and the metering channel with a liquid at the introduction pressure;
purging the liquid from the main channel by flowing a gas through the main channel while allowing the liquid to remain in the metering channel; and
injecting the liquid contained in the metering channel into the reaction well through the injection channel by creating a positive pressure higher than the introduction pressure in the main channel, or by creating a negative pressure in the reaction well, or by creating a positive pressure higher than the introduction pressure in the main channel and creating a negative pressure in the reaction well.

* * * * *